US012589022B2

(12) United States Patent
Abdelal et al.

(10) Patent No.: US 12,589,022 B2
(45) Date of Patent: Mar. 31, 2026

(54) FLUID COLLECTION ASSEMBLIES INCLUDING ONE OR MORE MOVEMENT ENHANCING FEATURES

(71) Applicant: PureWick Corporation, El Cajon, CA (US)

(72) Inventors: Dana Ahmad Abdelal, Marietta, GA (US); Nicolas Austerman, Atlanta, GA (US); Amanda Blackwell, Newborn, GA (US); Shaun Broussard, Conyers, GA (US); Jishen Cheng, Covington, GA (US); Rodrigo Fernandez, Loganville, GA (US); Eric Rehm, Greensboro, GA (US); Wendy Rodriguez, Covington, GA (US)

(73) Assignee: PureWick Corporation, Covington, GA (US)

( * ) Notice: Subject to any disclaimer, the term of this patent is extended or adjusted under 35 U.S.C. 154(b) by 750 days.

(21) Appl. No.: 17/912,147

(22) PCT Filed: Mar. 18, 2021

(86) PCT No.: PCT/US2021/023001
§ 371 (c)(1),
(2) Date: Sep. 16, 2022

(87) PCT Pub. No.: WO2021/188817
PCT Pub. Date: Sep. 23, 2021

(65) Prior Publication Data
US 2023/0138269 A1 May 4, 2023

Related U.S. Application Data

(60) Provisional application No. 62/991,754, filed on Mar. 19, 2020.

(51) Int. Cl.
*A61F 5/44* (2006.01)
*A61F 5/451* (2006.01)

(52) U.S. Cl.
CPC ............ *A61F 5/4404* (2013.01); *A61F 5/451* (2013.01)

(58) Field of Classification Search
CPC .......... A61F 5/455; A61F 5/451; A61F 5/453; A61F 5/4408; A61F 5/4404;
(Continued)

(56) References Cited

U.S. PATENT DOCUMENTS

| | | |
|---|---|---|
| 670,602 A | 3/1901 | Baker |
| 737,443 A | 8/1903 | Mooers |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)
(Continued)

*Primary Examiner* — Michele Kidwell
(74) *Attorney, Agent, or Firm* — Ballard Spahr LLP

(57) ABSTRACT

An example fluid collection assembly (100) includes a fluid impermeable barrier (102) defining at least one opening (104), a chamber (106) in fluid communication with the at least one opening (104), and at least one fluid outlet (108). The fluid collection assembly (100) also includes at least one porous material (110) disposed in the chamber (106). The fluid collection assembly (100) also includes at least one conduit (112) attached to the fluid outlet (108). The fluid collection assembly (100) includes one or more movement enhancing features (118).

20 Claims, 20 Drawing Sheets

(58) Field of Classification Search
CPC ...... A61F 5/4401; A61F 5/4405; A61F 5/441;
A61F 13/474; A61F 13/84; A61F 2/0009;
A61F 2005/4402; A61F 2013/8494; A61F
5/442; A61F 5/4556; A61F 5/48; A61F
5/44; A61F 6/08; A61F 2013/15146;
A61F 13/47227; A61M 2202/0496; A61M
2210/1092; A61B 10/007
See application file for complete search history.

(56) References Cited

U.S. PATENT DOCUMENTS

| 1,015,905 | A | 1/1912 | Northrop |
| 1,032,841 | A | 7/1912 | Koenig |
| 1,178,644 | A | 4/1916 | Johnson |
| 1,387,726 | A | 8/1921 | Karge |
| 1,742,080 | A | 12/1929 | Jones |
| 1,979,899 | A | 11/1934 | Obrien et al. |
| 2,241,010 | A | 5/1941 | Chipley |
| 2,262,772 | A | 11/1941 | Peder |
| 2,326,881 | A | 8/1943 | Packer |
| 2,379,346 | A | 6/1945 | Farrell |
| 2,485,555 | A | 10/1949 | Bester |
| 2,571,357 | A | 10/1951 | Charles |
| 2,613,670 | A | 10/1952 | Edward |
| 2,616,426 | A | 11/1952 | Adele |
| 2,644,234 | A | 7/1953 | Earl |
| 2,648,335 | A | 8/1953 | Chambers |
| 2,859,786 | A | 11/1958 | Tupper |
| 2,944,551 | A | 7/1960 | Carl |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,169,528 | A | 2/1965 | Knox et al. |
| 3,171,506 | A | 3/1965 | Therkel |
| 3,175,719 | A | 3/1965 | Herndon |
| 3,194,238 | A | 7/1965 | Breece |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | Mcguire et al. |
| 3,349,768 | A | 10/1967 | Keane |
| 3,362,590 | A | 1/1968 | Gene |
| 3,366,116 | A | 1/1968 | Huck |
| 3,398,848 | A | 8/1968 | Donovan |
| 3,400,717 | A | 9/1968 | Bruce et al. |
| 3,406,688 | A | 10/1968 | Bruce |
| 3,424,163 | A | 1/1969 | Gravdahl |
| 3,425,471 | A | 2/1969 | Yates |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,683,918 | A | 8/1972 | Pizzella |
| 3,699,815 | A | 10/1972 | Holbrook |
| 3,726,277 | A | 4/1973 | Hirschman |
| 3,742,952 | A | 7/1973 | Magers et al. |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,865,109 | A | 2/1975 | Elmore et al. |
| 3,881,486 | A | 5/1975 | Fenton |
| 3,881,489 | A | 5/1975 | Hartwell |
| 3,915,189 | A | 10/1975 | Holbrook et al. |
| 3,998,228 | A | 12/1976 | Poidomani |
| 3,999,550 | A | 12/1976 | Martin |
| 4,015,604 | A | 4/1977 | Csillag |
| 4,020,843 | A | 5/1977 | Kanall |
| 4,022,213 | A | 5/1977 | Stein |
| 4,027,776 | A | 6/1977 | Douglas |
| 4,064,962 | A | 12/1977 | Hunt |
| 4,096,897 | A | 6/1978 | Cammarata |
| 4,116,197 | A | 9/1978 | Bermingham |
| 4,180,178 | A | 12/1979 | Turner |
| 4,187,953 | A | 2/1980 | Turner |
| 4,194,508 | A | 3/1980 | Anderson |
| 4,200,102 | A | 4/1980 | Duhamel et al. |
| 4,202,058 | A | 5/1980 | Anderson |
| 4,203,503 | A | 5/1980 | Bertotti et al. |
| 4,209,076 | A | 6/1980 | Bertotti et al. |
| 4,223,677 | A | 9/1980 | Anderson |
| 4,233,025 | A | 11/1980 | Larson et al. |
| 4,233,978 | A | 11/1980 | Hickey |
| 4,246,901 | A | 1/1981 | Frosch et al. |
| 4,253,542 | A | 3/1981 | Ruspa et al. |
| 4,257,418 | A | 3/1981 | Hessner |
| 4,270,539 | A | 6/1981 | Frosch et al. |
| 4,281,655 | A | 8/1981 | Terauchi |
| 4,292,916 | A | 10/1981 | Bradley et al. |
| 4,330,239 | A | 5/1982 | Gannaway |
| 4,352,356 | A | 10/1982 | Tong |
| 4,360,933 | A | 11/1982 | Kimura et al. |
| 4,365,363 | A | 12/1982 | Windauer |
| 4,375,841 | A | 3/1983 | Vielbig |
| 4,387,726 | A | 6/1983 | Denard |
| 4,403,991 | A | 9/1983 | Hill |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,476,879 | A | 10/1984 | Jackson |
| 4,526,688 | A | 7/1985 | Schmidt et al. |
| 4,528,703 | A | 7/1985 | Kraus |
| D280,438 | S | 9/1985 | Wendt |
| 4,551,141 | A | 11/1985 | Mcneil |
| 4,553,968 | A | 11/1985 | Komis |
| 4,581,026 | A | 4/1986 | Schneider |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,769,215 | A | 9/1988 | Ehrenkranz |
| 4,771,484 | A | 9/1988 | Mozell |
| 4,772,280 | A | 9/1988 | Rooyakkers |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |

(56)               References Cited

U.S. PATENT DOCUMENTS

| | | | |
|---|---|---|---|
| 4,846,819 | A | 7/1989 | Welch |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,903,254 | A | 2/1990 | Haas |
| 4,904,248 | A | 2/1990 | Vaillancourt |
| 4,905,692 | A | 3/1990 | More |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |
| 5,112,324 | A | 5/1992 | Wallace |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,203,699 | A | 4/1993 | Mcguire |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,459 | A | 7/1994 | Lavon et al. |
| 5,340,840 | A | 8/1994 | Park et al. |
| 5,382,244 | A | 1/1995 | Telang |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,618,277 | A | 4/1997 | Goulter |
| 5,628,735 | A | 5/1997 | Skow |
| 5,636,643 | A | 6/1997 | Argenta et al. |
| 5,637,104 | A | 6/1997 | Ball et al. |
| 5,674,212 | A | 10/1997 | Osborn et al. |
| 5,678,564 | A | 10/1997 | Lawrence et al. |
| 5,678,654 | A | 10/1997 | Uzawa |
| 5,687,429 | A | 11/1997 | Rahlff |
| 5,695,485 | A | 12/1997 | Duperret et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |
| 5,865,378 | A | 2/1999 | Hollinshead et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| D409,303 | S | 5/1999 | Oepping |
| 5,911,222 | A | 6/1999 | Lawrence et al. |
| 5,957,904 | A | 9/1999 | Holland |
| 5,968,026 | A | 10/1999 | Osborn et al. |
| 5,972,505 | A | 10/1999 | Phillips et al. |
| 6,007,526 | A | 12/1999 | Passalaqua et al. |
| 6,039,060 | A | 3/2000 | Rower |
| 6,050,983 | A | 4/2000 | Moore et al. |
| 6,059,762 | A | 5/2000 | Boyer et al. |
| 6,063,064 | A | 5/2000 | Tuckey et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |

(56) References Cited

U.S. PATENT DOCUMENTS

| | | |
|---|---|---|
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |

(56) References Cited

U.S. PATENT DOCUMENTS

| | | | |
|---|---|---|---|
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,752,564 | B2 | 9/2017 | Arceno et al. |
| 9,788,992 | B2 | 10/2017 | Harvie |
| D804,907 | S | 12/2017 | Sandoval |
| 9,868,564 | B2 | 1/2018 | Mcgirr et al. |
| D814,239 | S | 4/2018 | Arora |
| D817,484 | S | 5/2018 | Lafond |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Villarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| D923,365 | S | 6/2021 | Wang |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,207,206 | B2 | 12/2021 | Sharma et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,890,221 | B2 | 2/2024 | Ulreich et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| D1,038,385 | S | 8/2024 | Ecklund et al. |
| 12,090,083 | B2 | 9/2024 | Ecklund et al. |
| 12,133,813 | B2 | 11/2024 | Ulreich et al. |
| 2001/0037097 | A1 | 11/2001 | Cheng et al. |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2003/0004436 | A1 | 1/2003 | Schmidt et al. |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0120178 | A1 | 6/2003 | Heki |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |

(56) References Cited

U.S. PATENT DOCUMENTS

| | | |
|---|---|---|
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |

(56)  References Cited

U.S. PATENT DOCUMENTS

| | | |
|---|---|---|
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042748 A1 | 2/2017 | Griffin |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |

(56) References Cited

U.S. PATENT DOCUMENTS

| | | |
|---|---|---|
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |
| 2024/0261131 A1 | 8/2024 | Garvey et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |

(56) References Cited

FOREIGN PATENT DOCUMENTS

| | | | |
|---|---|---|---|
| CA | 3098571 | A1 | 11/2019 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1602825 | A | 4/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 106132360 | A | 11/2016 |
| CN | 205849719 | U | 1/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 112566550 | A | 3/2021 |
| CN | 112603184 | A | 4/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| GB | 871820 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |

(56) References Cited

FOREIGN PATENT DOCUMENTS

| | | | |
|---|---|---|---|
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010058795 A | 3/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2016521191 A | 7/2016 |
| JP | 2017014698 A | 1/2017 |
| JP | 2017201272 A | 11/2017 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20090104426 A | 10/2009 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |

(56) References Cited

FOREIGN PATENT DOCUMENTS

| | | | |
|---|---|---|---|
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022031943 | A1 | 2/2022 |
| WO | 2022035745 | A1 | 2/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |

(56)          References Cited

FOREIGN PATENT DOCUMENTS

WO        2023244238 A1    12/2023
WO        2024058788 A1    3/2024

OTHER PUBLICATIONS

Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/051,585 mailed Oct. 8, 2024.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.

Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Oct. 10, 2023.
Final Office Action for U.S. Appl. No. 16/433,773 mailed Sep. 9, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,354 mailed Oct. 28, 2024.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/661,090 mailed Dec. 11, 2023.

(56) References Cited

OTHER PUBLICATIONS

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 17/808,354 mailed Apr. 10, 2024.

Final Office Action for U.S. Appl. No. 18/003,029 mailed Oct. 22, 2024.

Final Office Action for U.S. Appl. No. 18/134,857 mailed Jul. 25, 2024.

Final Office Action for U.S. Appl. No. 18/139,523 mailed Dec. 22, 2023.

Final Office Action for U.S. Appl. No. 18/140,163 mailed Mar. 27, 2024.

Final Office Action for U.S. Appl. No. 18/140,751 mailed Jan. 17, 2024.

Final Office Action for U.S. Appl. No. 18/164,800 mailed Dec. 6, 2023.

Final Office Action for U.S. Appl. No. 18/164,800 mailed Oct. 22, 2024.

Final Office Acton for U.S. Appl. No. 17/595,747 mailed Dec. 12, 2024.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

International Search Report and Written Opinion from International Application No. PCT/US2023/025192 mailed Feb. 7, 2024.

International Search Report and Written Opinion from International Application No. PCT/US2023/025939 mailed Feb. 7, 2024.

International Search Report and Written Opinion from International Application No. PCT/US2023/030365 mailed Mar. 13, 2024.

International Search Report and Written Opinion from International Application No. PCT/US2023/030373 mailed Mar. 13, 2024.

International Search Report and Written Opinion from International Application No. PCT/US2023/031433 mailed Mar. 4, 2024.

International Search Report and Written Opinion from International Application No. PCT/US2023/031740 mailed Mar. 4, 2024.

International Search Report and Written Opinion from International Application No. PCT/US2023/036238 mailed Jul. 22, 2024.

International Search Report and Written Opinion from International Application No. PCT/US2023/036868 mailed Jun. 5, 2024.

International Search Report and Written Opinion from International Application No. PCT/US2023/075507 mailed Jun. 13, 2024.

International Search Report and Written Opinion from International Application No. PCT/US2023/077168 mailed Jun. 24, 2024.

International Search Report and Written Opinion from International Application No. PCT/US2023/077208 mailed May 10, 2024.

International Search Report and Written Opinion from International Application No. PCT/US2023/080680 mailed Jul. 22, 2024.

International Search Report and Written Opinion from International Application No. PCT/US2023/085516 mailed Aug. 26, 2024.

Issue Notification for U.S. Appl. No. 16/245,726 mailed Oct. 18, 2023.

Issue Notification for U.S. Appl. No. 16/369,676 mailed Oct. 2, 2024.

Issue Notification for U.S. Appl. No. 16/449,039 mailed Jun. 19, 2024.

Issue Notification for U.S. Appl. No. 16/452,145 mailed Oct. 23, 2024.

Issue Notification for U.S. Appl. No. 17/051,550 mailed Mar. 13, 2024.

Issue Notification for U.S. Appl. No. 17/051,554 mailed Mar. 6, 2024.

Issue Notification for U.S. Appl. No. 17/326,980 mailed Jul. 10, 2024.

Issue Notification for U.S. Appl. No. 17/447,123 mailed Nov. 13, 2024.

Issue Notification for U.S. Appl. No. 17/448,811 mailed Jul. 3, 2024.

Issue Notification for U.S. Appl. No. 17/453,260 mailed Jul. 10, 2024.

Issue Notification for U.S. Appl. No. 17/453,560 mailed Aug. 7, 2024.

Issue Notification for U.S. Appl. No. 17/461,036 mailed Oct. 11, 2023.

Issue Notification for U.S. Appl. No. 17/657,474 mailed Jun. 19, 2024.

Issue Notification for U.S. Appl. No. 17/662,700 mailed Oct. 23, 2024.

Issue Notification for U.S. Appl. No. 17/663,046 mailed Dec. 20, 2023.

Issue Notification for U.S. Appl. No. 17/664,914 mailed Nov. 6, 2024.

Issue Notification for U.S. Appl. No. 17/667,097 mailed Dec. 11, 2024.

Issue Notification for U.S. Appl. No. 18/140,163 mailed Dec. 4, 2024.

Issue Notification for U.S. Appl. No. 18/198,464 mailed Nov. 20, 2024.

Issue Notification for U.S. Appl. No. 18/299,788 mailed Feb. 21, 2024.

Non-Final Office Action for U.S. Appl. No. 16/369,676 mailed Feb. 29, 2024.

Non-Final Office Action for U.S. Appl. No. 16/433,773 mailed Feb. 26, 2024.

Non-Final Office Action for U.S. Appl. No. 16/452,145 mailed Nov. 2, 2023.

Non-Final Office Action for U.S. Appl. No. 16/452,258 mailed Jun. 20, 2024.

Non-Final Office Action for U.S. Appl. No. 16/478,180 mailed Aug. 7, 2024.

Non-Final Office Action for U.S. Appl. No. 16/478,180 mailed Nov. 7, 2023.

Non-Final Office Action for U.S. Appl. No. 16/904,868 mailed Mar. 12, 2024.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,600 mailed Jan. 17, 2024.

Non-Final Office Action for U.S. Appl. No. 17/179,116 mailed Feb. 26, 2024.

Non-Final Office Action for U.S. Appl. No. 17/378,015 mailed Jul. 5, 2024.

Non-Final Office Action for U.S. Appl. No. 17/444,792 mailed Nov. 17, 2023.

Non-Final Office Action for U.S. Appl. No. 17/444,792 mailed Oct. 30, 2024.

Non-Final Office Action for U.S. Appl. No. 17/446,256 mailed Dec. 13, 2024.

Non-Final Office Action for U.S. Appl. No. 17/446,256 mailed Feb. 13, 2024.

Non-Final Office Action for U.S. Appl. No. 17/446,654 mailed Jun. 25, 2024.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/450,864 mailed May 29, 2024.

Non-Final Office Action for U.S. Appl. No. 17/451,345 mailed Jan. 17, 2024.

Non-Final Office Action for U.S. Appl. No. 17/451,345 mailed Jul. 25, 2024.

Non-Final Office Action for U.S. Appl. No. 17/451,354 mailed Apr. 4, 2024.

Non-Final Office Action for U.S. Appl. No. 17/453,560 mailed Oct. 16, 2023.

(56)        References Cited

OTHER PUBLICATIONS

Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Oct. 25, 2023.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/808,354 mailed Nov. 28, 2023.
Non-Final Office Action for U.S. Appl. No. 17/907,125 mailed Dec. 13, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 26, 2024.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/299,788 mailed Nov. 6, 2023.

(56)    References Cited

OTHER PUBLICATIONS

Notice of Allowance for U.S. Appl. No. 18/389,009 mailed Aug. 28, 2024.
Notice of Allowance for U.S. Appl. No. 18/426,795 mailed Nov. 20, 2024.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/878,268 mailed Sep. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 15/611,587, filed Jun. 1, 2017.
U.S. Appl. No. 17/013,822, filed Sep. 7, 2020.
U.S. Appl. No. 17/444,792, filed Aug. 10, 2021.
U.S. Appl. No. 17/451,719, filed Oct. 19, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.

U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/561,893, filed Dec. 11, 2023.
U.S. Appl. No. 63/568,615, filed Mar. 22, 2024.
U.S. Appl. No. 63/596,012, filed Nov. 3, 2023.
U.S. Appl. No. 63/608,553, filed Dec. 11, 2023.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/433,773 mailed Feb. 15, 2023.
Advisory Action for U.S. Appl. No. 17/662,700 mailed Jan. 30, 2023.
Final Office Action for U.S. Appl. No. 17/051,399 mailed Mar. 9, 2023.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/042725 mailed Dec. 19, 2022.
Non-Final Office Action for U.S. Appl. No. 17/444,792 mailed Feb. 10, 2023.
Non-Final Office Action for U.S. Appl. No. 17/448,811 mailed Mar. 1, 2023.
Non-Final Office Action on U.S. Appl. No. 16/904,868 mailed Mar. 15, 2023.
Non-Final Office Action on U.S. Appl. No. 17/655,464 mailed Mar. 14, 2023.
Notice of Allowance for U.S. Appl. No. 17/461,036 mailed Feb. 22, 2023.
Notice of Allowance for U.S. Appl. No. 17/663,046 mailed Jan. 30, 2023.
Restriction Requirement for U.S. Appl. No. 17/446,256 mailed Jan. 23, 2023.
U.S. Appl. No. 14/433,773, filed Apr. 3, 2020.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.

(56) References Cited

OTHER PUBLICATIONS

U.S. Appl. No. 18/164,800, filed Feb. 6, 2023.
U.S. Appl. No. 18/246,121, filed Mar. 21, 2023.
U.S. Appl. No. 63/308,190, filed Feb. 9, 2022.
Action for U.S. Appl. No. 14/722,613 mailed Mar. 4, 2019.
Action for U.S. Appl. No. 14/952,591 mailed Jun. 1, 2018.
Action for U.S. Appl. No. 15/238,427 mailed Apr. 10, 2019.
Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 17/662,700 mailed Sep. 30, 2022.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 malled Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.

(56)                References Cited

OTHER PUBLICATIONS

International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.

International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/044107 mailed Dec. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.

(56) References Cited

OTHER PUBLICATIONS

Non-Final Office Action for U.S. Appl. No. 14/952,591 malled Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 malled Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,550 mailed Dec. 15, 2022.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 17/451,345 mailed Dec. 7, 2022.
Non-Final Office Action for U.S. Appl. No. 17/662,700 mailed Jul. 22, 2022.
Non-Final Office Action for U.S. Appl. No. 29/624,661 mailed Jul. 18, 2019.
Non-Final Office Action for U.S. Appl. No. 29/694,002 mailed Jun. 24, 2020.

Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Oct. 6, 2022.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.

(56)            References Cited

OTHER PUBLICATIONS

U.S. Appl. No. 15/260,103, filed Sep. 8, 2016.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 18/003,029, filed Dec. 22, 2022.
U.S. Appl. No. 29/741,751, filed Jul. 15, 2020.

U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.

(56) References Cited

OTHER PUBLICATIONS

U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.

Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application": https://www.sciencedirect.com/science/article/abs/pil/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#IdivAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.

(56) References Cited

OTHER PUBLICATIONS

Dai , et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/ Urine-Collectors/Urine-Collection-Accessories/Male-Urinary-Pouch-External-Collection-Device.
Hollister , "Retracted Penis Pouch by Hollister", Vitality Medical. com, 6 pages.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/478,180 mailed Sep. 7, 2023.
Advisory Action for U.S. Appl. No. 17/051,550 mailed Sep. 8, 2023.
Final Office Action for U.S. Appl. No. 16/369,676 mailed Aug. 31, 2023.
Final Office Action for U.S. Appl. No. 16/478,180 mailed May 31, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/446,256 mailed Sep. 19, 2023.

Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Issue Notification for U.S. Appl. No. 16/899,956 mailed Mar. 29, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 17/051,399 mailed Aug. 18, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,751 mailed Sep. 14, 2023.

(56) References Cited

OTHER PUBLICATIONS

Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 18/299,788 mailed Jul. 24, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 17/664,487, filed May 23, 2022.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/548,152, filed Aug. 28, 2023.
U.S. Appl. No. 18/549,387, filed Sep. 7, 2023.
U.S. Appl. No. 63/150,640, filed Feb. 18, 2021.
*PureWick Corporation* v. *Sage Products, LLC* Transcripts vol. 2 , Mar. 29, 2022.
*PureWick Corporation* v. *Sage Products, LLC* Transcripts vol. 3 , Mar. 30, 2022.
*PureWick Corporation* v. *Sage Products, LLC* Transcripts vol. 4 , Mar. 31, 2022.
*PureWick Corporation* v. *Sage Products, LLC* Transcripts vol. 5 , Apr. 1, 2022.
*PureWick Corporation* v. *Sage Products, LLC* Transcripts vol. 1 , Mar. 28, 2022.
"AMXD Control Starter Kit" , Omni Medical Systems, Inc. , 1 page.
"AMXDmax Advanced Mission Extender Device User & Maintenance Guide" , Omni Medical , Jan. 11, 2010 , 10 pages.
"AMXDmax Development History 2002-2014" , Omni Medical Systems, Inc. , 2 pages.
"Combat Force Multiplier in Flight Bladder Relief Cockpit Essential Equipment Brochure" , Omni Medical , 20 pages.
"GSA Price List" , Omni Medical , Apr. 2011 , 2 pages.
"How is Polypropylene Fiber Made" , https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020 , 3 pages.
"Letter to Mark Harvie of Omni Measurement Systems" , Department of Veterans Affairs , Nov. 1, 2007 , 11 pages.
"Revised AMXDmax Advanced Mission Extender Device User & Maintenance Guide" , Omni Medical Systems , Oct. 8, 2019 , 52 pages.
Merriam-Webster Dictionary, , "Embed Definition & Meaning" , https://www.merriam-webster.com/dictionary/embed last accessed Aug. 3, 2023 , 2003.
Pieper , et al. , "An external urine-collection device for women: A clinical trial" , Journal of ER Nursing, vol. 20, No. 2 , Mar./Apr. 1993 , pp. 51-55.
Vinas , "A Solution For An Awkward—But Serious—Subject" , http://www.aero-news.net/index.cfm?do=main.textpost&id=69ae2bb1-838b-4098-a7b5-7flbb2505688 last accessed Feb. 8, 2021.

FLUID COLLECTION ASSEMBLIES INCLUDING ONE OR MORE MOVEMENT ENHANCING FEATURES

CROSS-REFERENCE TO RELATED APPLICATIONS

This application is a U.S. Nationalization of PCT International Application No. PCT/US2021/023001 filed on Mar. 18, 2021, which claims priority to U.S. Provisional Patent Application No. 62/991,754 filed on Mar. 19, 2020, the entire disclosure of each of which is incorporated herein, in its entirety, by this reference.

BACKGROUND

A person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes bodily fluids collection is needed for monitoring purposes or clinical testing.

Urinary catheters, such as a Foley catheter, can be used to address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

Embodiments are directed to bodily fluids collection assemblies that include one or more movement enhancing features along with systems including and methods of using such bodily fluids collection assemblies. In an embodiment, a fluid collection assembly is disclosed. The fluid collection assembly includes a fluid impermeable barrier. The fluid impermeable barrier defines at least one opening, a chamber in fluid communication with the at least one opening, and at least one fluid outlet. The fluid collection assembly also includes at least one porous material disposed in the chamber and at least one conduit attached to the at least one fluid outlet. Further, the fluid collection assembly includes one or more movement enhancing features configured to allow increased movement by an individual using the fluid collection assembly without significantly increasing a likelihood that the fluid collection assembly leaks.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
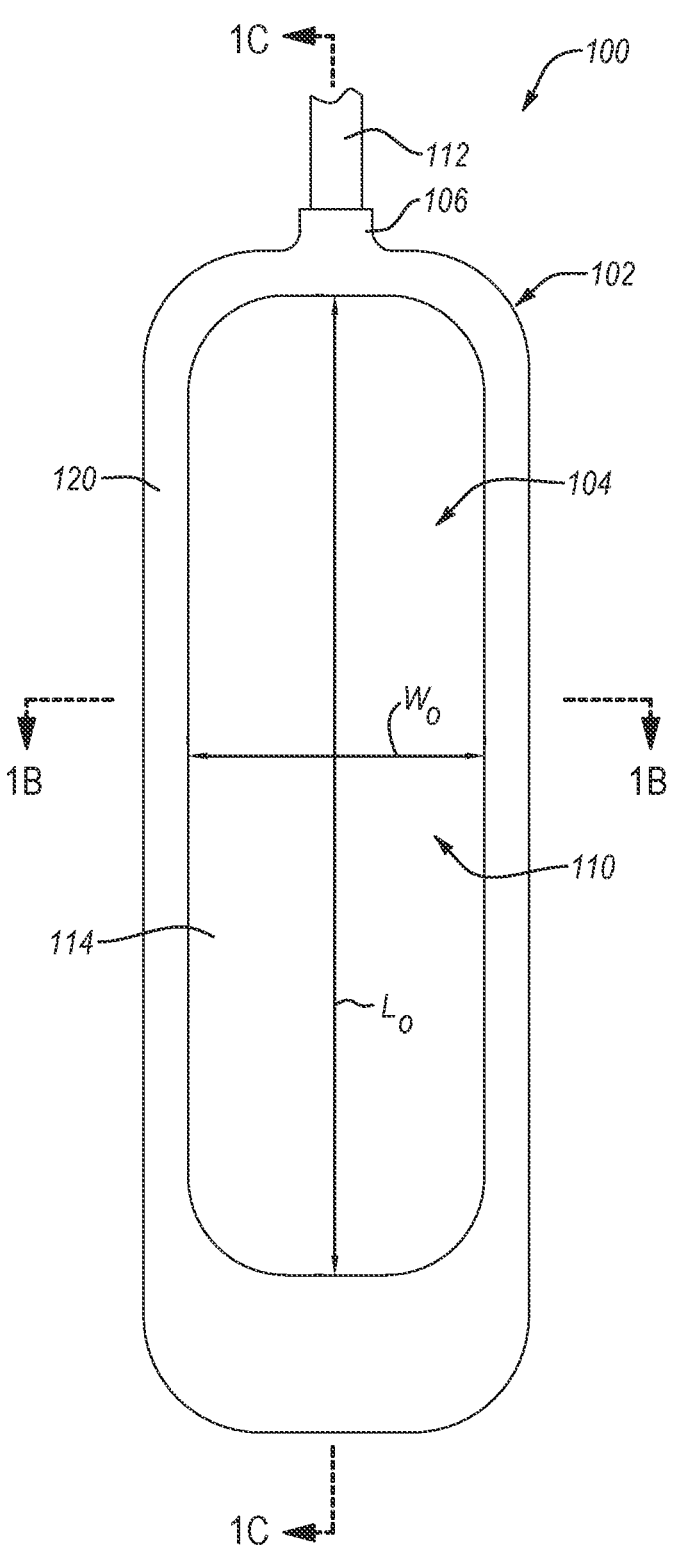
FIG. 1A is a top plan view of a fluid collection assembly that includes one or more movement enhancing features, according to an embodiment.

Embodiments are directed to bodily fluids collection assemblies that include one or more movement enhancing features along with systems including and methods of using such bodily fluids collection assemblies. An example fluid collection assembly includes a fluid impermeable barrier defining at least one opening, a chamber in fluid communication with the at least one opening, and at least one fluid outlet. The fluid collection assembly also includes at least one porous material (e.g., at least one wicking material) disposed in the chamber. The fluid collection assembly also includes at least one conduit attached to the fluid outlet. During operation, the fluid collection assembly may receive one or more bodily fluids (e.g., urine) from an individual through the opening and into the chamber. The porous material may receive at least some of the bodily fluids that enter the chamber. A suction applied from the conduit to the chamber may direct the bodily fluids that chamber towards the conduit. The conduit may then remove the bodily fluids from the chamber.

The fluid collection assembly includes one or more movement enhancing features. The one or more movement enhancing features are configured to allow increased movement of an individual using the fluid collection assemblies disclosed herein compared to conventional fluid collection assemblies (i.e., substantially similar fluid collection assemblies that do not include any of the movement enhancing features disclosed herein). In an example, the fluid collection assemblies disclosed herein may press against and/or be positioned around the urethral opening of the individual thereby allowing the fluid collection assemblies to receive bodily fluids discharged from the urethral opening. With conventional fluid collection assemblies, movement by the individual (e.g., walking or changing the individual's position) may cause the fluid collection assembly to shift which, in turn, may cause one or more passageways (e.g., gaps) to form between the conventional fluid collection assemblies and the individual. Bodily fluids may leak (e.g., fail to enter the chamber or, when bodily fluids were previously received in the chamber, flow out of the chamber through the opening) through these passageways. As such, with conventional fluid collection assemblies, movement of the individual may be discouraged to prevent the bodily fluids from leaking. However, the movement enhancing features disclosed herein may be configured to allow increased movement of the individual without causing leaks. For example, at least some of the movement enhancing features may prevent the fluid collection assemblies disclosed herein from shifting when the individual moves. As such, at least some of the movement enhancing features disclosed herein may prevent the formation of passageways caused by the fluid collection assemblies shifting when the individual moves thereby minimizing the likelihood that the individual's movement cause leaks. In an example, the movement enhancing features may include a portable vacuum source and/or fluid storage container such that the individual using the fluid collection assemblies disclosed herein are not tethered to a non-portable vacuum source and/or fluid storage container.

It is noted that any of the fluid collection assemblies disclosed herein may include any one or any combination of the movement enhancing features disclosed herein, without limitation.

Figure 1B:
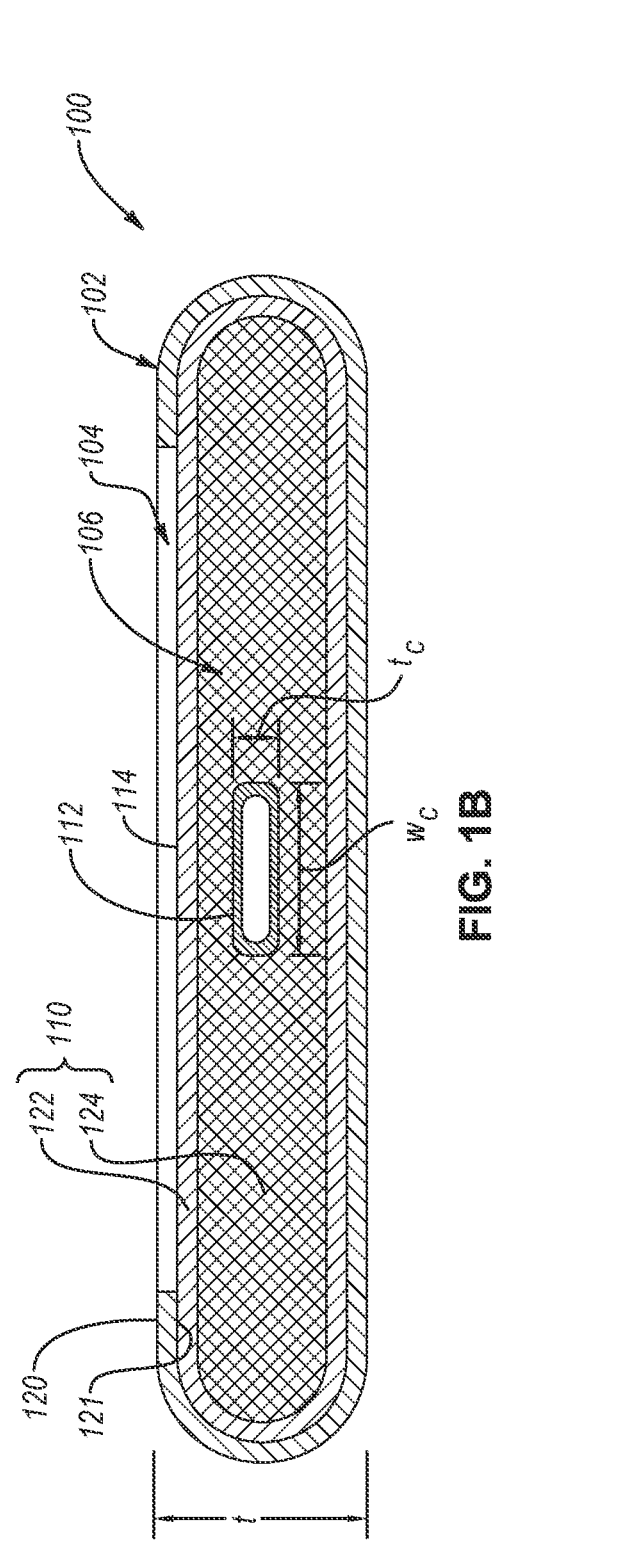
FIGS. 1B and 1C are cross-sectional views of the fluid collection assembly taken along line 1B-1B and 1C-1C, respectively, as shown in FIG. 1A.
Figure 1C:
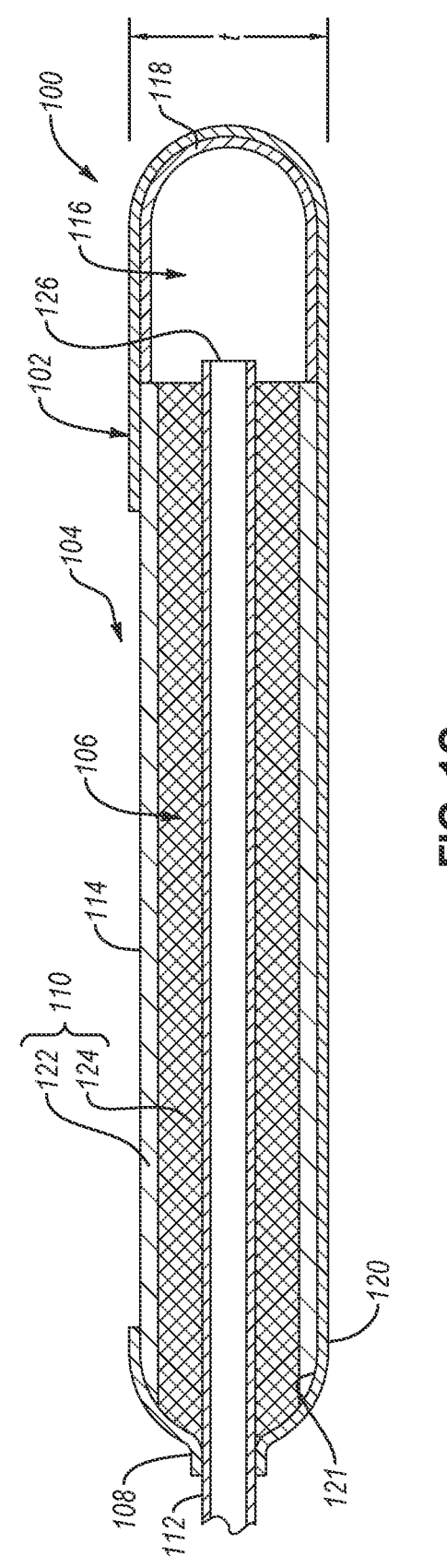

FIG. 1A is a top plan view of a fluid collection assembly 100 that includes one or more movement enhancing features, according to an embodiment. FIGS. 1B and 1C are cross-sectional views of the fluid collection assembly 100 taken along line 1B-1B and 1C-1C, respectively, as shown in FIG. 1A, according to an embodiment. The fluid collection assembly 100 includes a fluid impermeable barrier 102. The fluid impermeable barrier 102 defines at least one opening 104 configured to receive one or more bodily fluids from an individual. The fluid impermeable barrier 102 also defines a chamber 106 that is in fluid communication with the opening 104 and at least one fluid outlet 108. The fluid collection assembly 100 also include at least one porous material 110 disposed in the chamber 106 and at least one conduit 112 attached to the fluid outlet 108. The fluid collection assembly 100 also include one or more movement enhancing features.

The porous material 110 includes a contact surface 114. The contact surface 114 of the porous material 110 is the surface of the porous material 110 that extends across the opening 104 and, thus, is the surface of the porous material 110 that may contact the individual (e.g., contact or be positioned proximate to the urethral opening of the individual). In an embodiment, the contact surface 114 may be a movement enhancing feature of the fluid collection assembly 100 when the contact surface 114 is substantially flat, as shown in FIGS. 1B and 1C. For example, the vaginal region (collectively referred to as "vaginal region") exhibits generally flat and/or convex shape.

Some conventional fluid collection assemblies include a contact surface exhibiting a generally convex shape. The generally convex shape of the conventional fluid collection assemblies allow the contact surface thereof to press against labia folds of the individual and may even partially penetrate between the labia folds of the individual. However, lateral shifts in the conventional fluid collection assemblies (e.g., shifts in a direction perpendicular to a longitudinal length of the conventional fluid collection assemblies) caused by movement of the individual mitigates any benefit of the convex shape of the convex contact surface. In other words, the lateral shift of the conventional fluid collection assemblies caused by movement of the individual may cause leaks. In contrast, the substantially flat contact surface 114 of the porous material 110 of the fluid collection assembly 100 may continually press against the labia folds of the individual even when the fluid collection assembly laterally shifts. As such, the substantially flat contact surface 114 allows the individual to move without significantly increasing the risk of leaks. Further, the substantially flat contact surface 114 generally corresponds to the portions of the vaginal region that are substantially flat and is more easily bent into a concave shape that corresponds to the convex shape of the vaginal region than the conventional fluid collection assemblies. Causing the substantially flat contact surface 114 to corresponds to the shape of the vaginal region decreases the likelihood that the fluid collection assembly 100 shifts when the individual moves compared to the convention fluid collection assemblies.

The opening 104 may exhibit a maximum length Lo measured parallel to a longitudinal axis of the fluid collection assembly 100 and a maximum width $W_O$ measured perpendicularly to the maximum length $L_O$. In an embodiment, the opening 104 may form a movement enhancing feature of the fluid collection assembly 100 when a ratio of the maximum width $W_O$ relative to the maximum length $L_O$ (i.e., $W_O/L_O$) is about 0.35 or greater, such as about 0.4 or greater, about 0.45 or greater, about 0.5 or greater, about 0.55 or greater, about 0.6 or greater, about 0.65 or greater, about 0.7 or greater, about 0.75 or greater, about 0.8 or greater, about 0.85 or greater, about 0.9 or greater, about 0.95 or greater, about 1.0 or greater, or in ranges of about 0.35 to about 0.45, about 0.4 to about 0.5, about 0.45 to about 0.55, about 0.5 to about 0.6, about 0.55 to about 0.65, about 0.6 to about 0.7, about 0.65 to about 0.75, about 0.7 to about 0.8, about 0.75 to about 0.85, about 0.8 to about 0.9, about 0.85 to about 0.95, or about 0.9 to about 1.0. For example, the increased width $W_O$ of the opening 104 relative to the length $L_O$ allows the fluid collection assembly 100 to accommodate larger lateral shifts caused by the individual moving without significantly increasing the likelihood of leaks compared to conventional fluid collection assemblies.

In an embodiment, the one or more movement enhancing features includes forming the fluid collection assembly 100 to exhibit a high degree of flexibility. The high degree of flexibility of the fluid collection assembly 100 allows the contact surface 114 to correspond to the shape of the vaginal region. As previously discussed, the fluid collection assembly 100 is less likely to shift when the fluid collection assembly 100 exhibits a shape that corresponds to the shape of the vaginal region. Further, movement of the individual may cause the shape of the vaginal region to change. For example, an individual moving from a sitting position to a laying or standing position may cause the vaginal region to straighten and movement of the thighs of the individual may cause the vaginal region to be compressed or pulled. However, the high flexibility of the fluid collection assembly 100 allows the contact surface 114 to better conform to the changes of the shape of the vaginal region thereby allowing greater movement of the individual without significantly increasing the likelihood that the fluid collection assembly 100 leaks.

In an embodiment, the fluid collection assembly 100 exhibits a high degree of flexibility because the fluid collection assembly 100 exhibits a relatively small maximum thickness t since the flexibility of the fluid collection assembly 100 is directly proportional to the thickness t thereof. For example, conventional fluid collection assemblies may exhibit a maximum thickness of about 25 mm or greater. However, the fluid collection assembly 100 may exhibit a maximum thickness that is about 25 mm or less which allows the fluid collection assembly 100 to exhibit a flexibility that is greater than the conventional fluid collection assemblies. The increased flexibility may allow the fluid collection assembly 100 to better conform to the vaginal region when the individual moves than the conventional fluid collection assemblies. In an example, the fluid collection assembly 100 may exhibit a maximum thickness t that is about 22.5 mm or less, about 20 mm or less, about 17.5 mm or less, about 15 mm or less, about 12.5 mm or less, about 10 mm or less, about 8 mm or less, about 6 mm or less, about 5 mm or less, about 4 mm or less, about 3 mm or less, about 2 mm or less, about 1 mm or less, or in ranges of about 1 mm to about 3 mm, about 2 mm to about 4 mm, about 3 mm to about 5 mm, about 4 mm to about 6 mm, about 5 mm to about 8 mm, about 6 mm to about 10 mm, about 8 mm to about 12.5 mm, about 10 mm to about 15 mm, about 12.5 mm to about 17.5 mm, about 15 mm to about 20 mm, about 17.5 mm to about 22.5 mm, or about 20 mm to about 25 mm.

The thickness t of the fluid collection assembly 100 may be selected based on the amount of movement that the individual is expected to make. In an example, the thickness t of the fluid collection assembly 100 may be about 10 mm to about 20 mm when the fluid collection assembly 100 is configured to allow limited movement of the individual, such as minor movement (e.g., adjusting the position of the thighs) while the individual remains in a constant position (e.g., remains laying down or remains sitting). In an example, the thickness t of the fluid collection assembly 100 may be about 5 mm to about 15 mm when the fluid collection assembly 100 is configured to allow the individual to change their position, such as allowing the individual to change between a laying position and a sitting position. In an example, the thickness t of the fluid collection assembly 100 may be about 1 mm to about 10 mm when the fluid collection assembly 100 is configured to be used while the individual walks.

The fluid collection assembly 100 exhibits a generally flat elongated shape that may allow the fluid collection assembly 100 to fit, at least partially, in the space and/or folds between the thighs, the perineum, and the vaginal region. The ability of the fluid collection assembly 100 to fit, at least partially, in the space and/or folds between the thighs, the perineum, and the vaginal region may allow the fluid collection assembly 100 exhibit the thickness t that is about 25 mm or less due to the relative shape of the fluid collection assembly 100. Additionally, the ability of the fluid collection assembly 100 to fit, at least partially, in the space and/or folds between the thighs, the perineum, and the vaginal region may allow the fluid collection assembly 100 to exhibit a maximum width (measured between opposing outer surfaces of the fluid impermeable barrier 102) that is about 25 mm or greater, unlike at least some conventional fluid collection assemblies which may exhibit a maximum width that is about 25 mm. For example, the fluid collection assembly 100 may exhibit a maximum width that is about 30 mm or greater, about 40 mm or greater, about 50 mm or greater, about 60 mm or greater, about 70 mm or greater, about 80 mm or greater, about 90 mm or greater, about 100 mm or greater, or in ranges of about 25 mm to about 40 mm, about 30 mm to about 50 mm, about 40 mm to about 60 mm, about 50 mm to about 70 mm, about 60 mm to about 80 mm, about 70 mm to about 90 mm, or about 80 mm to about 100 mm. The larger maximum width of the fluid collection assembly 100 allows the opening 104 to exhibit the relatively large width $W_O$ relative to the length $L_O$ of the opening 104.

The conduit 112 may exhibit a relatively flat cross-sectional shape due to the relatively small thickness t of the fluid collection assembly 100. For example, the conduit 112 may exhibit a conduit width $W_C$ and a conduit thickness $t_C$ measured perpendicularly to the conduit width $W_C$. Due to the relatively flat cross-sectional shape of the conduit 112, the conduit width $W_C$ may be greater than the conduit thickness $t_C$ thereby allowing the conduit 112 to be able to remove sufficient quantities of bodily fluids from the chamber 106. The smaller conduit thickness $t_C$ relative to the conduit width $W_C$ may allow the conduit 112 to extend within the chamber 106 and behind the porous material 110 from the fluid outlet 108 to the fluid reservoir 116.

As previously discussed, the fluid collection assembly 100 may exhibits a highly flexibility. In an embodiment, the fluid collection assembly 100 exhibits the high flexibility thereof by decreasing the thickness of the fluid impermeable barrier 102 since the flexibility of the fluid collection assembly 100 depends, in part, on thickness of the fluid impermeable barrier 102. For example, at least some conventional fluid collection assemblies include a fluid impermeable barrier 102 exhibiting at thickness that is about 1 mm or greater. However, in some of the embodiments disclosed herein, the fluid impermeable barrier 102 may exhibit a thickness that is about 0.9 mm or less, about 0.8 mm or less, about 0.7 mm or less, about 0.6 mm or less, about 0.5 mm or less, about 0.4 mm or less, about 0.3 mm or less, about 0.2 mm or less, about 0.1 mm or less, or in ranges of about 0.05 mm to about 0.2 mm, about 0.1 mm to about 0.3 mm, about 0.2 mm to about 0.4 mm, about 0.3 mm to about 0.5 mm, about 0.4 mm to about 0 6 mm, about 0.5 mm to about 0.7 mm, about 0.6 mm to about 0.8 mm, about 0.7 mm to about 0.9 mm. The thickness of the fluid impermeable barrier 102 may depend on several factors. In an example, the thickness of the fluid impermeable barrier 102 may be selected based on the amount of movement that the fluid collection assembly 100 is configured to allow. For instance, the thickness of the fluid impermeable barrier 102 may be about 0.7 mm to about 0.9 mm when the fluid collection assembly 100 allows limited movement, about 0.3 mm to about 0.7 mm when the fluid collection assembly 100 allows the individual to changes between a standing, a sitting, and/or a lying position, or about 0.3 mm or less when the fluid collection assembly is configured to be used while the individual walks.

In an example, the thickness of the fluid impermeable barrier 102 may be selected based on the maximum thickness of the fluid collection assembly 100.

Referring to FIG. 1C, the fluid collection assembly 100 may include a fluid reservoir 116 that is a substantially unoccupied portion of the chamber 106. The fluid reservoir 116 may be defined between the fluid impermeable barrier 102 and porous material 110. The bodily fluids that are in the chamber 106 may flow through the porous material 110 to the fluid reservoir 116 and the fluid reservoir 116 may retain of the bodily fluids therein. In an embodiment, when the fluid collection assembly 100 exhibits a high flexibility, the portion of the fluid impermeable barrier 102 defining the fluid reservoir 116 may collapse since the high flexibility of the fluid collection assembly 100 may not provide enough support to maintain the shape of the fluid impermeable barrier 102. Collapsing the fluid impermeable barrier 102 may decrease the volume of the bodily fluids that may be held in the fluid reservoir 116 and may cause the fluid impermeable barrier 102 to at least partially obstruct the conduit 112. As such, in an embodiment, the movement enhancing features of the fluid collection assembly 100 may include a fluid reservoir reinforcement structure 118. The fluid reservoir reinforcement structure 118 is configured to provide additional structure to the portions of the fluid impermeable barrier 102 that define the fluid reservoir 116, thereby preventing or inhibiting the fluid impermeable barrier 102 from collapsing.

In an embodiment, the fluid reservoir reinforcement structure 118 is formed by increasing the thickness of the portion of the fluid impermeable barrier 102 that defines the fluid reservoir 116 relative to the rest of the fluid impermeable barrier 102. Increasing the thickness of the fluid impermeable barrier 102 increases the rigidity of the fluid impermeable barrier 102 and may inhibit the fluid impermeable barrier 102 from collapsing. In an embodiment, as shown, the fluid reservoir reinforcement structure 118 is distinct from the fluid impermeable barrier 102. In such an embodiment, the fluid reservoir reinforcement structure 118 may be formed from the same material or one or more different materials that the portion of the fluid impermeable barrier 102 that defines the fluid reservoir 116. When the fluid reservoir reinforcement structure 118 is formed from the same material as the fluid impermeable barrier 102, the fluid reservoir reinforcement structure 118 effectively increases the thickness of the portion of the fluid impermeable barrier 102 that defines the fluid reservoir 116. When the fluid reservoir reinforcement structure 118 is formed from a material that is different than the fluid impermeable barrier 102, the fluid reservoir reinforcement structure 118 may be formed from a material exhibiting an elasticity (i.e., Young's modulus) that is greater than the fluid impermeable barrier 102. Examples of material that may exhibit an elasticity greater than the rest of the fluid impermeable barrier 102 includes epoxy, acetal, polyester, a metal (e.g., a metal foil), or any other suitable material. Since the fluid reservoir reinforcement structure 118 is formed from a different material than the fluid impermeable barrier 102, the fluid reservoir reinforcement structure 118 may be attached to the fluid impermeable barrier 102 using any suitable technique, such as with an adhesive, ultrasonic welding, heat staking, etc.

In an embodiment, when the fluid reservoir reinforcement structure 118 is distinct from the fluid impermeable barrier 102, the fluid reservoir reinforcement structure 118 may be disposed on (e.g., attached to) an outer surface 120 of the fluid impermeable barrier 102 or may be disposed on (e.g., attached to) an inner surface 121 of the fluid impermeable barrier 102.

As previously discussed, the fluid impermeable barrier 102 at least partially defines the opening 104 and the chamber 106 (e.g., interior region). For example, at least one inner surface 121 of the fluid impermeable barrier 102 at least partially defines the chamber 106 within the fluid collection assembly 100. The fluid impermeable barrier 102 temporarily stores the bodily fluids in the chamber 106. The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface 120 of the fluid impermeable barrier 102 may be formed from a soft and/or smooth material, thereby reducing chaffing. During use, a portion of the outer surface 120 of the fluid impermeable barrier 102 may contact the wearer. The fluid impermeable barrier 102 may be sized and shaped to fit in the gluteal cleft between the legs of an individual.

The opening 104 provides an ingress route for bodily fluids to enter the chamber 106. The opening 104 may be defined by the fluid impermeable barrier 102 such as by an inner edge of the fluid impermeable barrier 102. For example, the opening 104 is formed in and extends through the fluid impermeable barrier 102, from the outer surface 120 to the inner surface 121, thereby enabling the bodily fluids to enter the chamber 106 from outside of the fluid collection assembly 100. In an embodiment, the opening 104 may be an elongated hole (the length $L_O$ is more than 50% greater than the width $W_O$) in the fluid impermeable barrier 102. For example, the opening 104 may be defined as a cut-out in the fluid impermeable barrier 102. The opening 104 may be located and shaped to be positioned adjacent to a female urethral opening.

The fluid collection assembly 100 may be positioned proximate to the female urethral opening and urine may enter the chamber 106 of the fluid collection assembly 100 via the opening 104. The fluid collection assembly 100 is configured to receive the bodily fluids into the chamber 106 via the opening 104. When in use, the opening 104 may extend from a first location above the urethral opening (e.g., at or near the top of the urethral opening or the pubic hair) to a second location below the urethral opening (e.g., at or near the anus or the vaginal opening).

In some examples, as previously discussed, the fluid impermeable barrier 102 may define an fluid outlet 108 sized to receive the conduit 112. The at least one conduit 112 may be disposed in the chamber 106 or otherwise in fluid communication with the chamber 106 via the fluid outlet 108. The fluid outlet 108 may be sized and shaped to form an at least substantially fluid tight seal against the conduit 112 or the at least one tube thereby substantially preventing the bodily fluids from escaping the chamber 106.

The fluid impermeable barrier 102 may include markings thereon (not shown), such as one or more markings to aid a user in aligning the fluid collection assembly 100 on the wearer. For example, a line on the fluid impermeable barrier 102 (e.g., opposite the opening 104) may allow a healthcare professional to align the opening 104 over the urethral opening of the individual wearing the fluid collection assembly 100. In examples, the markings may include one or more of alignment guide or an orientation indicator, such as a stripe or hashes. Such markings may be positioned to align the fluid collection assembly 100 to one or more anatomical features such as a pubic bone, etc.

As previously discussed, the fluid collection assembly 100 includes porous material 110 disposed in the chamber 106. The porous material 110 may cover at least a portion (e.g., all) of the opening 104. The porous material 110 is exposed to the environment outside of the chamber 106 through the opening 104. The permeable properties referred to herein may be wicking, capillary action, absorption, diffusion, or other similar properties or processes, and are referred to herein as "permeable" and/or "porous." The porous material 110 may also wick the bodily fluids generally towards an interior of the chamber 106, as discussed in more detail below. The porous material 110 may include one or more of a fluid permeable membrane 122 or a fluid permeable support 124.

In an embodiment, at least a portion of the porous material 110 may be a wicking material configured to wick and/or allow transport any of the bodily fluids away from the opening 104, thereby preventing bodily fluids from escaping the chamber 106. The porous material 110 may not include absorption of the bodily fluids into at least a portion of the wicking material. Put another way, substantially no absorption or solubility of the bodily fluids into the porous material may take place after the porous material is exposed to the bodily fluids. While no absorption is desired, the term "substantially no absorption" may allow for nominal amounts of absorption and/or solubility of the bodily fluids into the porous material (e.g., absorbency), such as about 30 wt % of the dry weight of the wicking material, about 20%, about 10%, about 7 wt %, about 5 wt %, about 3 wt %, about 2 wt %, about 1 wt %, or about 0.5 wt % of the dry weight of the wicking material. In an embodiment, the porous material 110 may include at least one absorbent or adsorbent material.

The fluid collection assembly 100 may include the fluid permeable membrane 122 disposed in the chamber 106. The fluid permeable membrane 122 may cover at least a portion (e.g., all) of the opening 104. The fluid permeable membrane 122 may be composed to pull/push the bodily fluids away from the opening 104, thereby preventing the bodily fluids from escaping the chamber 106.

The fluid permeable membrane 122 may include any material that may be permeable to the bodily fluids. For example, the fluid permeable membrane 122 may include fabric, such as a gauze (e.g., a silk, linen, or cotton gauze), another soft fabric, another smooth fabric, or any of the other porous material disclosed herein. Forming the fluid permeable membrane 122 from gauze, soft fabric, and/or smooth fabric may reduce chaffing caused by the fluid collection assembly 100.

The fluid collection assembly 100 may include the fluid permeable support 124 disposed in the chamber 106. The fluid permeable support 124 is configured to support the fluid permeable membrane 122 since the fluid permeable membrane 122 may be formed from a relatively foldable, flimsy, or otherwise easily deformable material. For example, the fluid permeable support 124 may be positioned such that the fluid permeable membrane 122 is disposed between the fluid permeable support 124 and the fluid impermeable barrier 102. As such, the fluid permeable support 124 may support and maintain the position of the fluid permeable membrane 122. The fluid permeable support 124 may include any material that may be permeable to the bodily fluids, such as any of the fluid permeable membrane materials disclosed herein above. For example, the fluid permeable membrane material(s) may be utilized in a more dense or rigid form than in the fluid permeable membrane 122 when used as the fluid permeable support 124. The fluid permeable support 124 may be formed from any fluid permeable material that is less deformable than the fluid permeable membrane 122. For example, the fluid permeable support 124 may include a porous polymer (e.g., nylon, polyester, polyurethane, polyethylene, polypropylene, etc.) structure (e.g., spun fibers such as spun nylon fibers) or an open cell foam. In some examples, the fluid permeable support 124 may be formed from a natural material, such as cotton, wool, silk, or combinations thereof. In such examples, the material may have a coating to prevent or limit absorption of the bodily fluids into the material, such as a water repellent coating. In some examples, the fluid permeable support 124 may be formed from fabric, felt, gauze, or combinations thereof. In some examples, the fluid permeable membrane 122 may be optional. For example, the porous material 110 may include only the fluid permeable support 124. In some examples, the fluid permeable support 124 may be optionally omitted from the fluid collection assembly 100. For example, the porous material 110 may only include the fluid permeable membrane 122.

In an embodiment, the fluid permeable membrane 122 and the fluid permeable support 124 are wicking materials. In such an embodiment, the fluid permeable support 124 may have a greater ability to wick the bodily fluids than the fluid permeable membrane 122, such as to move the bodily fluids inwardly from the outer surface 120 of the fluid collection assembly 100. In some examples, the wicking ability of the fluid permeable support 124 and the fluid permeable membrane 122 may be substantially the same.

In an embodiment, not shown, the fluid permeable membrane 122 and the fluid permeable support 124 may at least substantially completely fill the portions of the chamber 106 that are not occupied by the conduit 112. In an embodiment, as previously discussed, the fluid permeable membrane 122 and the fluid permeable support 124 may not substantially completely fill the portions of the chamber 106 that are not occupied by the conduit 112. In such an example, the fluid collection assembly 100 includes the fluid reservoir 116 disposed in the chamber 106.

The fluid reservoir 116 is a substantially unoccupied portion of the chamber 106. The fluid reservoir 116 may be defined between the fluid impermeable barrier 102 and one or both of the fluid permeable membrane 122 and fluid permeable support 124.

The bodily fluids that are in the chamber 106 may flow through the fluid permeable membrane 122 and/or fluid permeable support 124 to the fluid reservoir 116. The fluid reservoir 116 may retain of the bodily fluids therein. The bodily fluids that are in the chamber 106 may flow through the fluid permeable membrane 122 and/or fluid permeable support 124 and, optionally, to the fluid reservoir 116. The fluid impermeable barrier 102 may retain the bodily fluids in the fluid reservoir 116. The fluid reservoir 116 may be located in a portion of the chamber 106 that is designed to be located in a gravimetrically low point of the fluid collection assembly when the device is worn.

In an embodiment, not shown, the conduit 112 may be at least partially disposed in the chamber 106. The conduit 112 may be used to remove fluid form the chamber 106. The conduit 112 (e.g., a tube) includes the inlet 126 and an outlet (not shown) positioned downstream from the inlet 126. The outlet may be operably coupled to a suction source, such as a vacuum pump for withdrawing the bodily fluids form the chamber through the conduit 112. The conduit 112 fluidly couples the chamber 106 with the fluid storage container (fluid storage container 1692 shown in FIG. 16 or the vacuum source (vacuum source 1664 shown in FIG. 16

The conduit 112 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 112 may include silicon or latex. In some examples, the conduit 112 may include one or more portions that are resilient, such as to by having one or more of a diameter or wall thickness that allows the conduit to be flexible.

In an example, the conduit 112 is configured to be at least insertable into the chamber 106. In such an example, the conduit 112 may include one or more markers (not shown) on an exterior thereof that are located to facilitate insertion of the conduit 112 into the chamber 106. For example, the conduit 112 may include one or more markings thereon that are configured to prevent over or under insertion of the conduit 112, such as when the conduit 112 defines an inlet 126 that is configured to be disposed in or adjacent to the reservoir. In another example, the conduit 112 may include one or more markings thereon that are configured to facilitate correct rotation of the conduit 112 relative to the chamber 106. The one or more markings may include a line, a dot, a sticker, or any other suitable marking.

As described in more detail below, the conduit 112 is configured to be coupled to, and at least partially extend between, one or more of the fluid storage container (not shown) and the vacuum source (not shown). In an example, the conduit 112 is configured to be directly connected to the vacuum source (not shown). In such an example, the conduit 112 may extend from the fluid impermeable barrier 102 by at least one foot, at least two feet, at least three feet, or at least six feet. In another example, the conduit 112 is configured to be indirectly connected to at least one of the fluid storage container (not shown) and the vacuum source (not shown). In some examples, the conduit 112 is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 126 and the outlet of the conduit 112 are configured to fluidly couple (e.g., directly or indirectly) the vacuum source (not shown) to the chamber 106 (e.g., the reservoir). As the vacuum source (FIG. 16) applies a vacuum/suction in the conduit 112, the bodily fluids in the chamber 106 may be drawn into the inlet 126 and out of the fluid collection assembly 100 via the conduit 112. In some examples, the conduit 112 may be frosted or opaque (e.g., black) to obscure visibility of the bodily fluids therein.

Figure 2A:
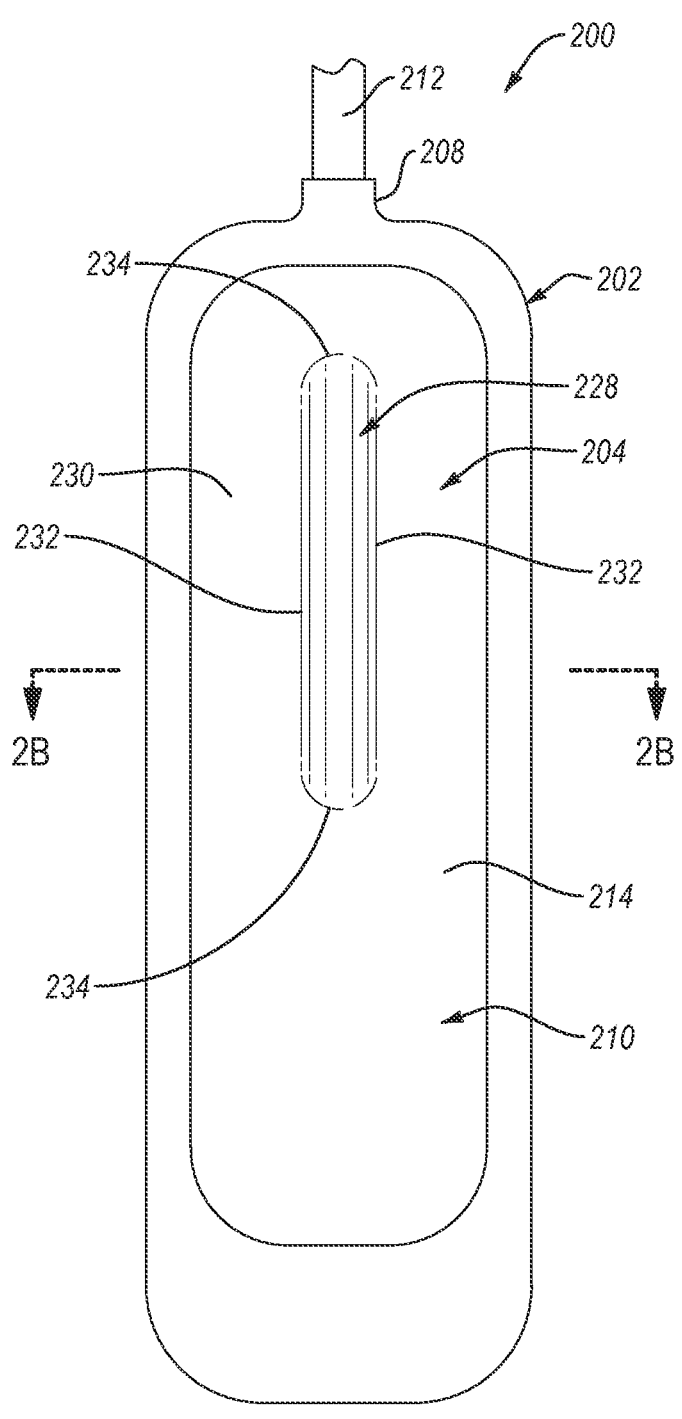
FIG. 2A is a top plan view of a fluid collection assembly including a contact surface that is not flat, according to an embodiment.
Figures 2B, 3:
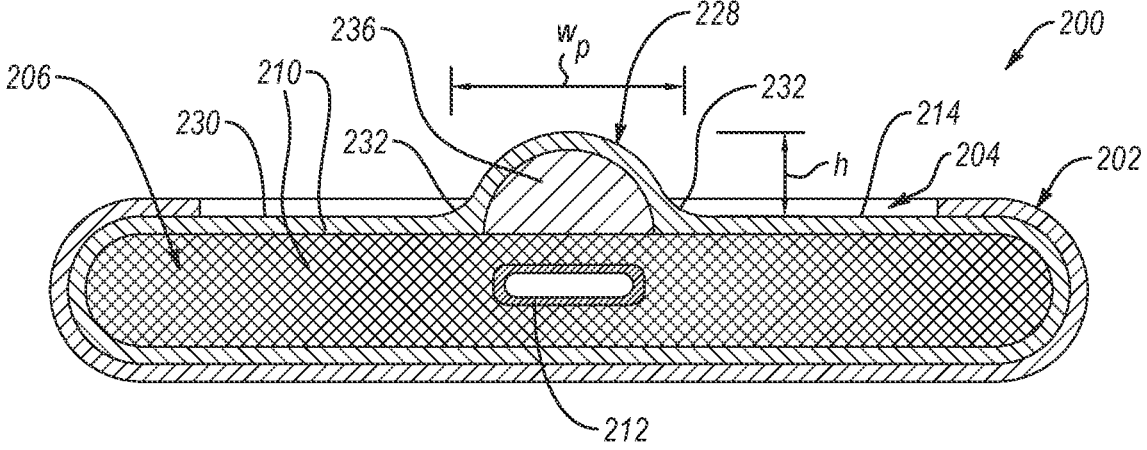
FIG. 2B is a cross-sectional view of the fluid collection assembly taken along line 2B-2B, as shown in FIG. 2A.
FIG. 3 is a cross-sectional view of a fluid collection assembly that includes a protrusion that extends substantially completely across the opening thereof, according to an embodiment.

The fluid collection assemblies disclosed herein may include a contact surface that is not substantially flat. For example, FIG. 2A is a top plan view of a fluid collection assembly 200 including a contact surface 214 that is not flat, according to an embodiment. FIG. 2B is a cross-sectional view of the fluid collection assembly 200 taken along line 2B-2B, as shown in FIG. 2A, according to an embodiment. Except as otherwise disclosed herein, the fluid collection assembly 200 may be the same or substantially similar to any of the fluid collection assemblies disclosed herein. For example, the fluid collection assembly 200 may include a fluid impermeable barrier 202 defining an opening 204, a chamber 206, and a fluid outlet 208. The fluid collection assembly 200 may also include a porous material 210 defining the contact surface 214 that extends across the opening 204 and a conduit 212.

As previously discussed, the contact surface 214 is not substantially flat. Instead, the contact surface 214 exhibits a protrusion 228. The sharp protrusion 228 extends from the rest of the contact surface 214 and is configured to press against and at least partially fit between the labia folds. As such, the protrusion 228 may prevent the formation of or minimize the likelihood that the labia folds form passageways through which the bodily fluids may leak. Further, the protrusion 228 may maintain the position of the fluid collection assembly 200 relative to the vaginal region even when the individual moves. Thus, the protrusion 228 may be movement enhancing feature of the fluid collection assembly 200.

The protrusion 228 exhibits a height h and a width $W_P$. The height h and the width $W_P$ of the protrusion 228 are selected to allow the protrusion 228 to fit between the labia folds of the individual. In an example, the height h may be about 25 mm or less or less, about 20 mm or less or less, about 15 mm or less, about 10 mm or less, about 5 mm or less, or in ranges of about 5 mm to about 10 mm, about 7.5 mm to about 12 5 mm, about 10 mm to about 15 mm, about 12.5 mm to about 17.5 mm, about 15 mm to about 20 mm, about 17.5 mm to about 22.5 mm, or about 20 mm to about 25 mm. In an example, the width $W_P$ is about 50 mm or less, about 40 mm or less, about 30 mm or less, about 20 mm or less, about 10 mm or less, or in ranges of about 10 mm to about 20 mm, about 15 mm to about 25 mm, about 20 mm to about 30 mm, about 25 mm to about 35 mm, about 30 mm to about 40 mm, about 35 mm to about 45 mm, or about 40 mm to about 50 mm. The protrusion 228 exhibiting any of the above height h and width $W_P$ may be sufficient to press against the labia folds and, in some embodiments, may be at least partially positionable between the labia folds. It is noted that the width $W_P$ may be greater than 50 mm, for example when the protrusion 228 tapers (as shown), without affecting the protrusions 228 ability to be at least partially positionable between the labia folds.

The height h and the width $W_P$ of the protrusion 228 may be selected based on a number of factors. In an embodiment, the height h of the protrusion 228 may be selected based on the width $W_P$ of the protrusion 228. For example, the height h and the Width $W_P$ of the protrusion 228 may be selected such that the protrusion 228 exhibits a generally semi-circular shape (e.g., the height h is about half the width $W_P$) or such that the height h is greater than half the width $W_P$ since a protrusion 228 exhibiting such heights h and widths $W_P$ may be better able to fit between the labia folds than a protrusion 228 exhibiting a height h that is less than half the width $W_P$. In another example, the height h and the Width $W_P$ of the protrusion 228 may be selected such that the height h is less than half the width $W_P$ since such a protrusion 228 may be more comfortable than other protrusions. In an embodiment, the height h and the width $W_P$ may be selected based on the size of the individual and/or the size of the fluid collection assembly 200 (as will be discussed in more detail with regards to FIGS. 11 and 12)

In an embodiment, the contact surface 214 includes the protrusion 228 and a flat portion 230. The contact surface 214 may exhibit the benefits of the protrusion 228 and the flat surfaces discussed above when the contact surface 114 includes both the protrusion 228 and the flat portion 230. For example, the protrusion 228 may prevent the formation of passageways through which the bodily fluids may leak and may inhibit the fluid collection assembly 200 from shifting while the individual moves. The flat portion 230 may mitigate the effect of the fluid collection assembly 200 laterally shifting. The flat portion 230 at least partially encloses the protrusion 228. In an example, the flat portion 230 may enclose at least one of the lateral sides 232 of the protrusion 228. In such an example, the flat portion 230 may mitigate the effects of laterally shifting the fluid collection assembly 200. In an example, the flat portion 230 may enclose at least one of the longitudinal sides 234 of the protrusion 228 (e.g., the protrusion 228 does not extend the whole length of the opening 204). In such an example, the protrusion 228 may be configured to be only positioned against or between the labia folds since the protrusion 228 may be uncomfortable when the protrusion 228 presses against other portions of the vaginal region.

In an embodiment, referring to FIG. 2B, the protrusion 228 may be formed may including an additional material 236 in the porous material 210. The additional material 236 increases the thickness of the porous material 210 thereby forming the protrusion 228. In an example, as illustrated, the additional material 236 is positioned between the fluid permeable membrane 222 and the fluid permeable support 224, thereby allowing the fluid permeable membrane 222 to contact the vaginal region. However, it is noted that the additional material 236 may be positioned between the fluid permeable support 224 and the conduit 212 or may be positioned on the fluid permeable membrane 222 such that the additional material 236 contacts the vaginal region. The additional material 236 may be formed from any of the porous materials disclosed herein thereby allowing the additional material 236 to receive bodily fluids and direct the bodily fluids towards the fluid reservoir (not shown). In an embodiment, the protrusion 228 may be formed by increasing the thickness of the fluid permeable membrane 222 and/or the fluid permeable support 224.

In an embodiment, any of the fluid collection assemblies disclosed herein may include a protrusion that extends substantially completely across the opening thereof. FIG. 3 is a cross-sectional view of a fluid collection assembly 300 that includes a protrusion 328 that extends substantially completely across the opening 304 thereof, according to an embodiment. Except as otherwise disclosed herein, the fluid collection assembly 300 may be the same or substantially similar to any of the fluid collection assemblies disclosed herein. For example, the fluid collection assembly 300 may include a fluid permeable barrier 302 defining the opening 304 and a chamber 306. The fluid collection assembly 300 also includes a porous material 310 disposed in the chamber 306 that forms a contact surface 314.

The contact surface 314 includes the protrusion 328. Unlike the protrusion 228 illustrated in FIGS. 2A and 2B, the protrusion 328 may exhibit a relatively wide width $W_{WP}$ that is greater than 50 mm. For example, as shown, the protrusion 328 may exhibit a wide width $W_{WP}$ that extends substantially completely across the opening 304. The wide width $W_{WP}$ may prevent the protrusion 328 from being positionable between the labia folds. However, the protrusion 328 may still press against the labia folds to minimize the passageways formed by the labia folds. Thus, the protrusion 328 may be a movement enhancing feature. Also, the protrusion 328 may be more comfortable than the protrusion 228 due to the wider width of the protrusion 328 relative to the protrusion 228.

Figure 4A:
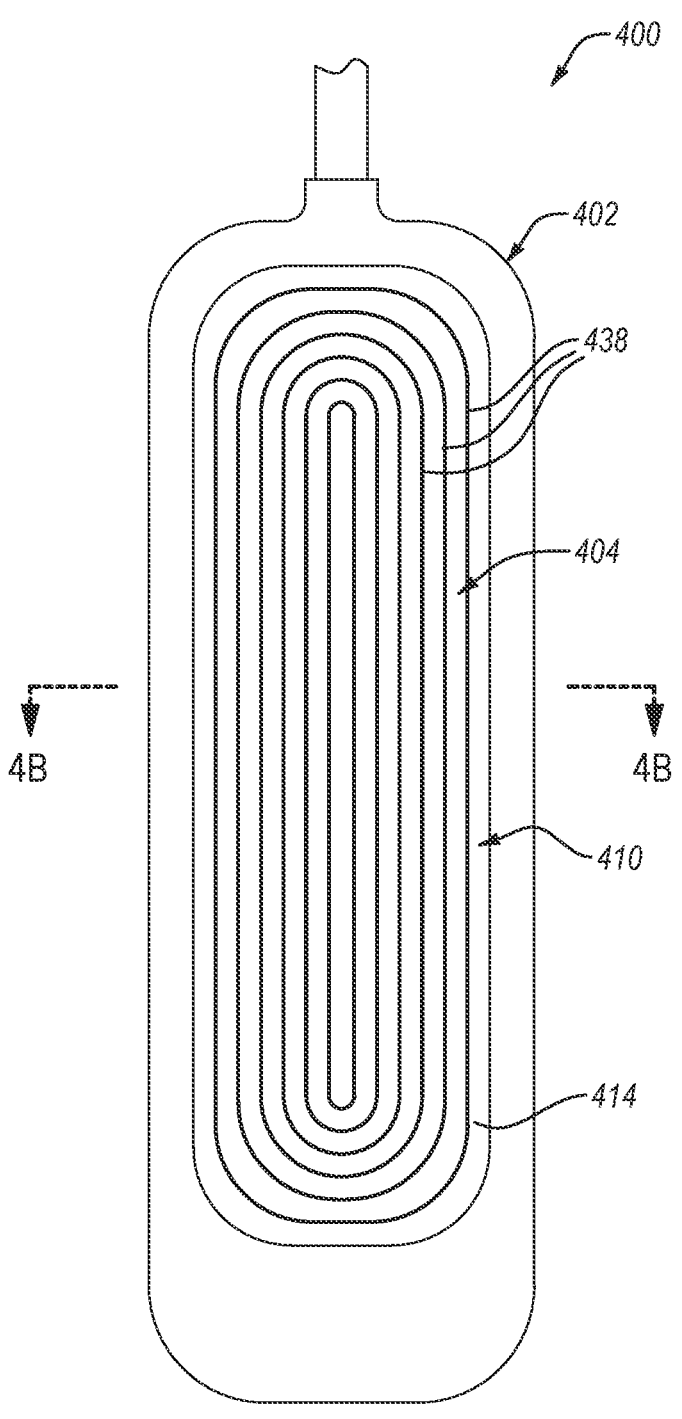
FIG. 4A is a top plan view of a fluid collection assembly that one or more grooves formed in the porous material that are movement enhancing features, according to an embodiment.
Figure 4B:
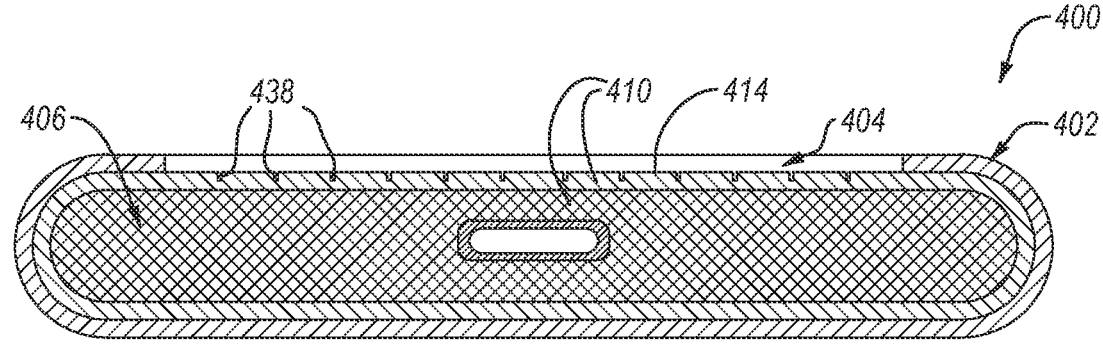
FIG. 4B is a cross-sectional view of the fluid collection assembly taken along line 4B-4B shown in FIG. 4B.

FIG. 4A is a top plan view of a fluid collection assembly 400 that includes one or more grooves 438 formed in the porous material 410 that are movement enhancing features, according to an embodiment. FIG. 4B is a cross-sectional view of the fluid collection assembly 400 taken along line 4B-4B shown in FIG. 4B, according to an embodiment. Except as otherwise disclosed herein, the fluid collection assembly 400 may be the same or substantially similar to any of the fluid collection assemblies disclosed herein. For example, the fluid collection assembly 400 may include a fluid impermeable barrier 402 defining an opening 404 and a chamber 406. The fluid collection assembly 400 may also include at least one porous material 410 disposed in the chamber 406 that defines a contact surface 414.

As previously discussed, the porous material 410 defines one or more grooves 438. The grooves 438 are movement enhancing features that are better able to grip the vaginal region since the grooves 438 increase the friction between the contact surface 414 and the vaginal region. Thus, the grooves 438 inhibit movement of the fluid collection assembly 400 when the individual moves. Additionally, the grooves 438 increase the surface area of the contact surface 414 thereby increasing the amount of bodily fluids that contact and may flow through the contact surface 414 at any given time.

In an embodiment, the grooves 438 are formed by decreasing the thickness of at least a portion of the porous material 410. For example, when the porous material 410 includes a fluid permeable membrane 422, the grooves 438 may be formed by selectively decreasing the thickness of portions of the fluid permeable membrane 422. In an embodiment, the grooves 438 may be formed by compressing a selected portion of the porous material 410. In such an embodiment, the grooves 438 may be formed by selectively sewing seams into porous material 410, selectively compressing portions of the porous material 410 and using an adhesive or heat (e.g., melting a portion of the porous material 410) to maintain the compressed shape, or any other suitable technique for compressing a selected portion of the porous material 410. In an embodiment, the grooves 438 are formed between ridges that extend from the rest of the porous material 410, wherein the grooves 438 are the space between adjacent ridges.

In an embodiment, as shown, the grooves 438 may form concentric annular shapes. The concentric annular shapes may be generally oval (as shown), generally circular, an irregular shape (e.g., an irregular curved shape), or any other suitable shape. In an embodiment, the grooves 438 may include one or more connected or non-connected lines, such as one or more curved lines. In an embodiment, the grooves 438 may form a network of interconnected grooves 438.

The grooves 438 may exhibit a depth and a width. The depth and the width of the grooves 438 may be about 0.1 mm to about 0.3 mm, about 0.2 mm to about 0.4 mm, about 0.3 mm to about 0.5 mm, about 0.4 mm to about 0.6 mm, about 0.5 mm to about 0.75 mm, about 0.7 mm to about 1 mm, about 0.75 mm to about 1.25 mm, about 1 mm to about 1.5 mm, about 1.25 mm to about 1.75 mm, about 1.5 mm to about 2 mm, about 1.75 mm to about 2.5 mm, or about 2 mm to about 3 mm. The depth and the width of the grooves 438 may be selected based on the size of the contact surface 414 and the number of grooves 438 formed in the contact surface 414.

Figure 5A:
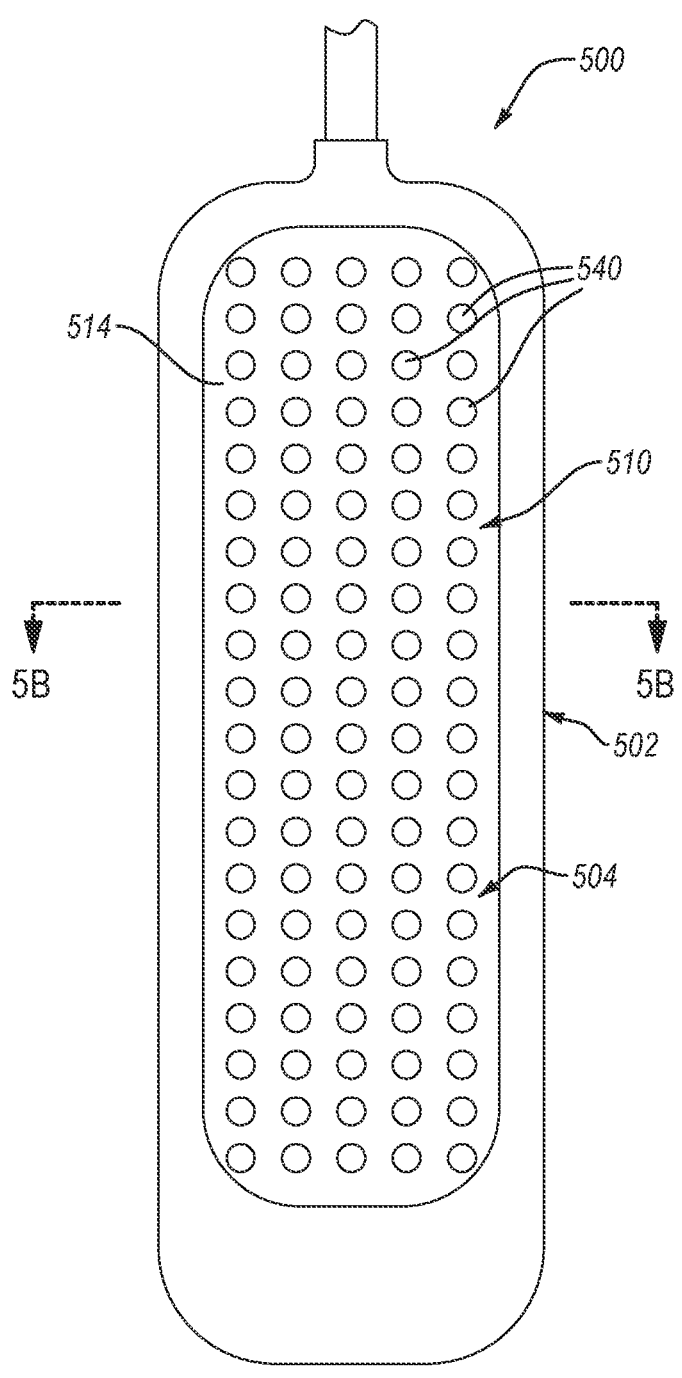
FIG. 5A is a top plan view of a fluid collection assembly that one or more perforations formed in the porous material that are movement enhancing features, according to an embodiment.
Figure 5B:
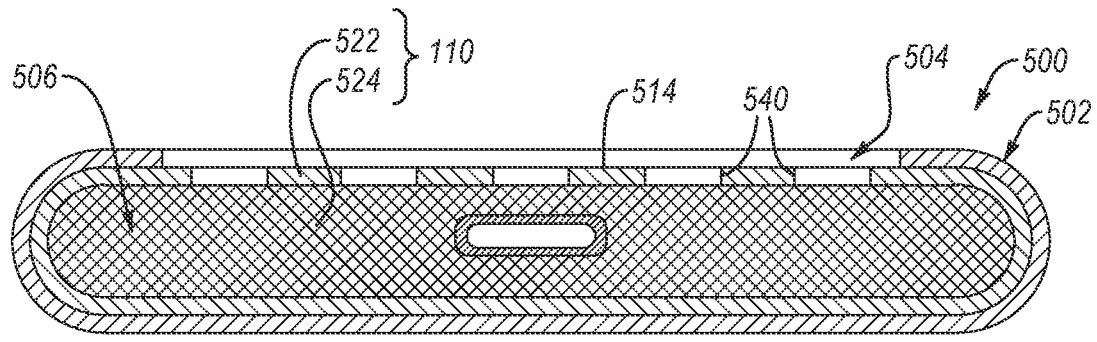
FIG. 5B is a cross-sectional view of the fluid collection assembly taken along line 5B-5B shown in FIG. 5B.

The movement enhancing features of the fluid collection assemblies disclosed herein may include perforations formed in the porous material instead of or in conjunction with any of the other movement enhancing features disclosed herein. FIG. 5A is a top plan view of a fluid collection assembly 500 that one or more perforations 540 formed in the porous material 510 that are movement enhancing features, according to an embodiment. FIG. 5B is a cross-sectional view of the fluid collection assembly 500 taken along line 5B-5B shown in FIG. 5B, according to an embodiment. Except as otherwise disclosed herein, the fluid collection assembly 500 may be the same or substantially similar to any of the fluid collection assemblies disclosed herein. For example, the fluid collection assembly 500 may include a fluid impermeable barrier 502 defining an opening 504 and a chamber 506. The fluid collection assembly 500 may also include at least one porous material 510 disposed in the chamber 506 that defines a contact surface 514.

As previously discussed, the porous material 510 defines one or more perforations 540. The perforations 540 are movement enhancing features because the perforations 540 allow the contact surface 514 to better grip the vaginal region since the perforations 540 increase the friction between the contact surface 514 and the vaginal region. Thus, the perforations 540 inhibit movement of the fluid collection assembly 500 when the individual moves. Additionally, the perforations 540 increase the surface area of the contact surface 514, thereby increasing the amount of bodily fluids that contact and may flow through the contact surface 514 at any given time.

The perforations 540 are distinct from the inherent porosity of the porous material 510. For example, the perforations 540 may exhibit an average maximum dimension (e.g., diameter) that is about 0.25 mm or greater, such as about 0.5 mm or greater, about 0.75 mm or greater, about 1 mm or greater, about 1.5 mm or greater, about 2 mm or greater, or in ranges of about 0.25 mm to about 0.75 mm, about 0.5 mm to about 1 mm, about 0.75 mm to about 1.5 mm, or about 1 mm to about 2 mm. As such, the perforations 540 are easily visible. Meanwhile, the average maximum dimension of the inherent porosity of the porous material 510 are significantly less than the perforations 540, such as exhibiting an average maximum dimension that is smaller than the average maximum dimensions of the perforations 540 by about 50% or more, about 75% or more, about 100% or more, about 150% or more, about 200% or more, about 300% or more, about 400% or more, about 500% or more, about 750% or more, or about 1000% or more.

As previously discussed, the porous material 510 may include a fluid permeable membrane 522 and a fluid permeable support 524. In an embodiment, as illustrated, at least one of the perforations 540 may extend completely through the fluid permeable membrane 522. In such an embodiment, the perforations 540 may allow the bodily fluids to more quickly flow through the fluid permeable membrane 522 thereby increasing the rate at which the porous material 510 may receive the bodily fluids. In an embodiment, at least one of the perforations 540 only extends partially through the fluid permeable membrane 522, such as recesses or dimples formed in the fluid permeable membrane 522. In such an embodiment, the perforations 540 may still allow the bodily fluids to more quickly flow through the fluid permeable membrane 522. In an embodiment, at least one of the perforations 540 may extend completely through the fluid permeable membrane 522 and at least partially through the fluid permeable support 524. In such an embodiment, the perforations 540 may allow the bodily fluids to flow more quickly through the porous material 510 but may also increase the likelihood that the bodily fluids leak from the chamber 506.

Figure 6A:
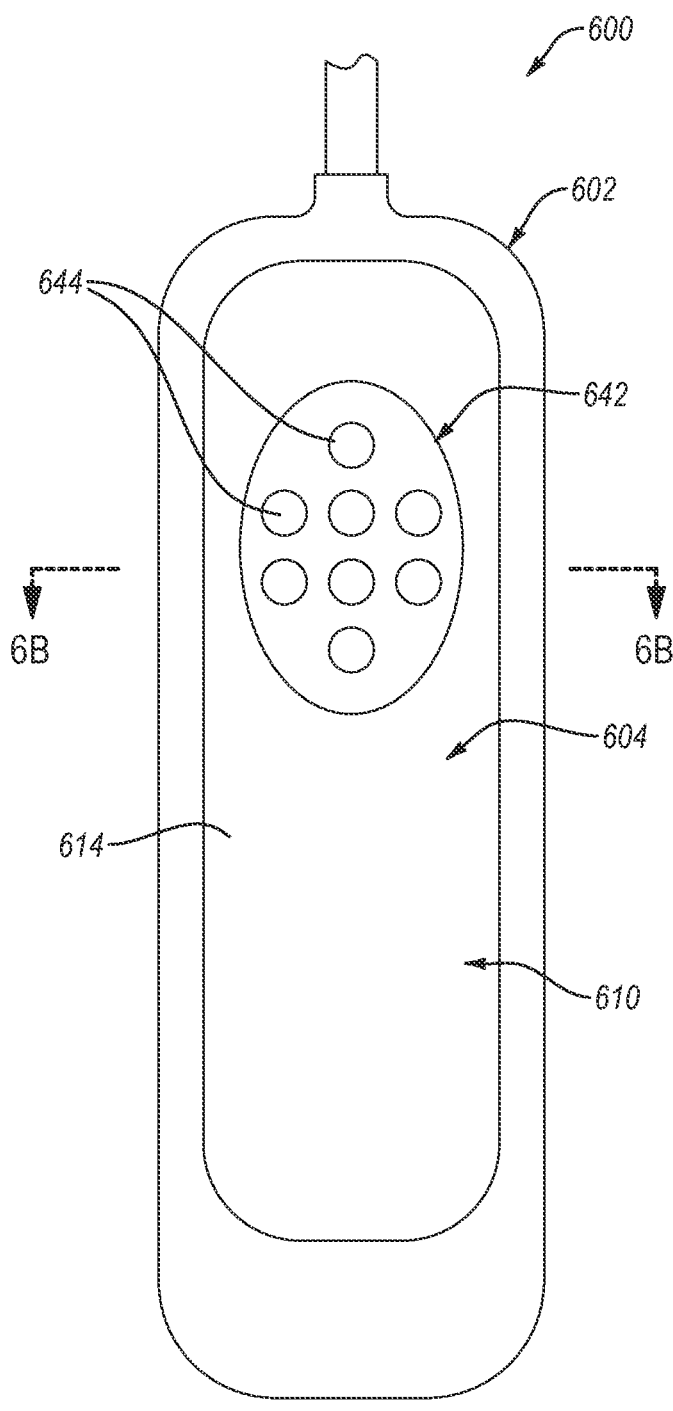
FIG. 6A is a top plan view of a fluid collection assembly that includes a fluid permeable element, according to an embodiment.
Figure 6B:
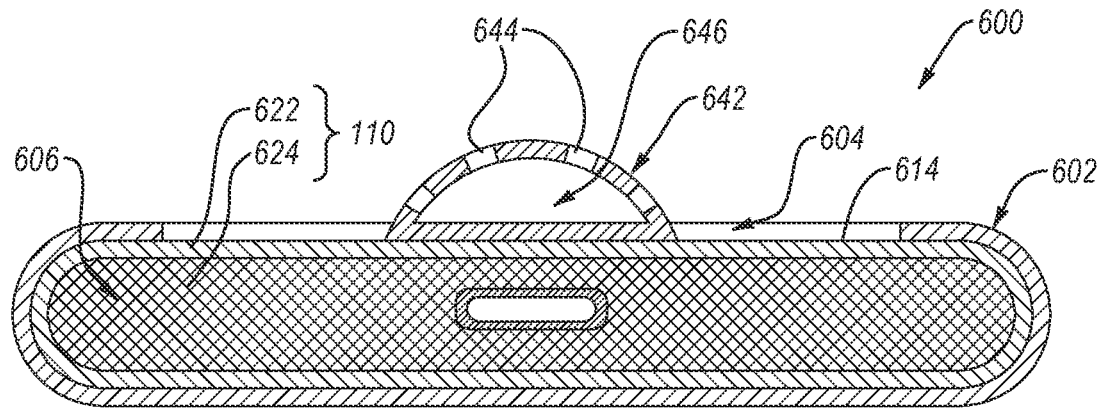
FIG. 6B is a cross-sectional view of the fluid collection assembly taken along line 6B-6B shown in FIG. 6A.

The movement enhancing features illustrated and discussed in FIGS. 2A-5B are formed in the porous material thereof. However, the movement enhancing features may be formed from a fluid permeable element that is distinct from and attached to the porous material. FIG. 6A is a top plan view of a fluid collection assembly 600 that includes a fluid permeable element 642, according to an embodiment. FIG. 6B is a schematic cross-sectional view of the fluid collection assembly 600 taken along line 6B-6B shown in FIG. 6A, according to an embodiment. Except as otherwise disclosed herein the fluid collection assembly 600 is the same or substantially similar to any of the fluid collection assemblies disclosed herein. For example, the fluid collection assembly 600 may include a fluid impermeable barrier 602 defining an opening 604 and a chamber 606. The fluid collection assembly 600 may also include a porous material 610 disposed in the chamber 606 that defines a contact surface 614 extending across the opening 604.

As previously discussed, the fluid collection assembly 600 includes a fluid permeable element 642 that is distinct from and attached to the porous material 610. In an embodiment, the fluid permeable element 642 may be harder and/or more rigid than the porous material 610. As such, the fluid permeable element 642 may be less likely to compress or otherwise deform compared to the porous material 610 since compressing or otherwise deforming the porous material 610 may limit the functionality of the porous material 610. For example, referring to the fluid collection assembly 200 illustrated in FIGS. 2A and 2B, the protrusion 228 may be compressed while attempting to position the protrusion 228 between the labia folds of the individual which may diminish the movement enhancing features of the protrusion 228 and limit the protrusion's 228 ability to receive bodily fluids. However, referring back to FIGS. 6A and 6B, the fluid permeable element 642 may be more easily positioned between the labia folds without compressing compared to the fluid permeable element 642.

In an embodiment, the fluid permeable element 642 may be harder and/or more rigid than the porous material 610 because the fluid permeable element 642 is formed from a material exhibiting a Young's modulus that is greater than the Young's modulus of the material that forms at least a portion of the porous material 610.

Examples of such materials include silicone. In an embodiment, the fluid permeable element 642 may be harder and/or more rigid than the porous material 610 because the fluid permeable element 642 is formed from a non-porous material or exhibits a porosity that is less than the porous material 610.

The fluid permeable element 642 may define one or more apertures 644 extending therethrough, such as when the fluid permeable element 642 is formed from a non-porous material. The apertures 644 may allow the bodily fluids to flow through the fluid permeable element 642.

In an embodiment, the fluid permeable element 642 defines a hollowed region 646. The hollowed region 646 may be substantially unoccupied space (as shown) or may be occupied by an additional porous material. Similar to the porous material 610, the additional porous material may direct the flow of any bodily fluids that enter the hollowed region 646 towards the porous material 610 thereby inhibiting leaks. The additional porous material may be formed from any of the porous materials disclosed herein. For example, the additional porous material may be formed from the same material as at least a portion of the porous material 610.

The fluid permeable element 642 may be attached to the porous material 610 using any suitable method. In an embodiment, as shown, the fluid permeable element 642 is attached directly to the contact surface 614 such that the fluid permeable element 642 directly contacts the vaginal region during operation. In such an embodiment, the fluid permeable element 642 may be attached to the porous material 610 via an adhesive, stitching, heat staking, or any other suitable technique. In an embodiment, the fluid permeable element 642 may be attached to the porous material 610 by disposing at least a portion of the fluid permeable element inside the porous material 610. For example, the fluid permeable element 642 may be disposed between the fluid permeable membrane 622 and the fluid permeable support 624 or the porous material 610 may define a pocket (not shown) that is configured to receive the fluid permeable element 642. As such, the porous material 610 contacts the vaginal region which may make the fluid collection assembly 600 more comfortable to use than if the fluid permeable element 642 directly contacts the vaginal region. It is noted that the fluid permeable element 642 may still be attached to the porous material 610 (e.g., via an adhesive, stitching, heat staking, etc.) even when the fluid permeable element 642 is disposed in the porous material 610 to prevent the fluid permeable element 642 from moving within the porous material 610.

The fluid permeable element 642 may form and/or include any of the movement enhancing features disclosed herein. For example, the fluid permeable element 642 may form a flat surface, a protrusion exhibiting a width of about 25 mm or less, a protrusion exhibiting a width of about 25 mm or more, one or more grooves, or one or more perforations therein.

Figure 7:
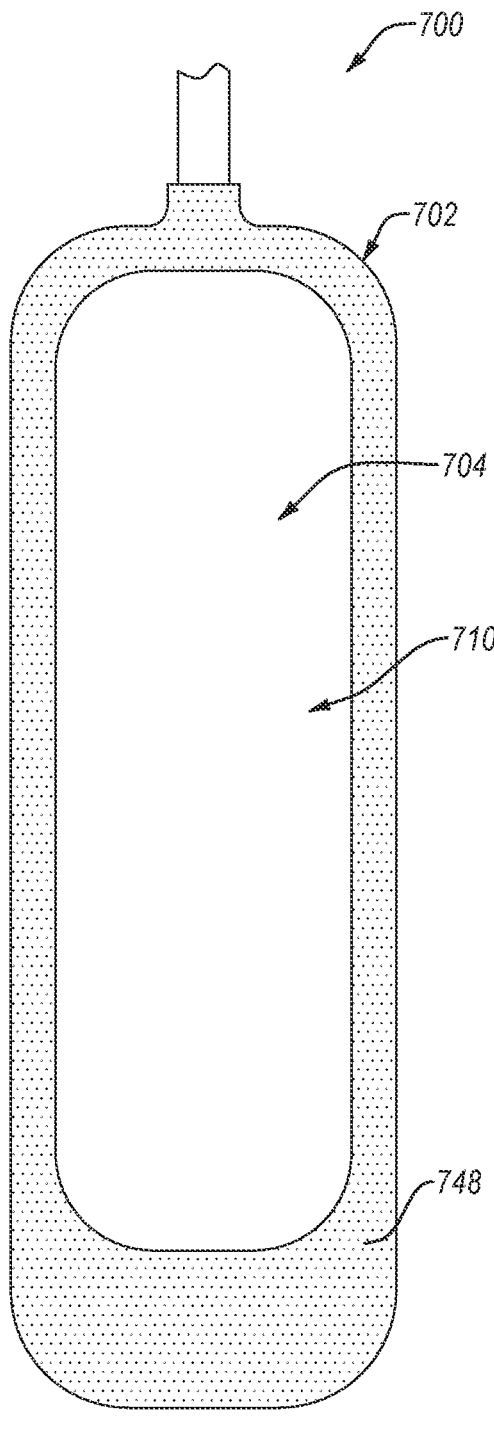
FIG. 7 is a top plan view of a fluid collection assembly that includes a fluid impermeable barrier having one or more movement enhancing features, according to an embodiment.

The fluid impermeable barriers of any of the fluid collection assemblies disclosed herein may include a movement enhancing feature. FIG. 7 is a top plan view of a fluid collection assembly 700 that includes a fluid impermeable barrier 702 having one or more movement enhancing features, according to an embodiment. Except as otherwise disclosed herein, the fluid collection assembly 700 is the same or substantially similar to any of the fluid collection assemblies disclosed herein. For example, the fluid impermeable barrier 702 of the fluid collection assembly 700 may define an opening 704 and a chamber (not shown). The fluid collection assembly 700 may also include a porous material 710 disposed in the chamber.

The fluid impermeable barrier 702 includes a textured surface 748. The textured surface 748 of the fluid impermeable barrier 702 allows the fluid impermeable barrier 702 to better grip the vaginal region thereby inhibiting movement of the fluid collection assembly 700 relative to the vaginal region when the individual moves. In an embodiment, as shown, the textured surface 748 of the fluid impermeable barrier 702 includes a plurality of bumps extending from the rest of the fluid impermeable barrier 702. The average diameter of the plurality of bumps may be selected to be about 3 mm or less, about 2 mm or less, about 1 mm or less, about 0.5 mm or less, about 0.1 mm or less, or in ranges of about 0.1 mm to about 1 mm, about 0.5 mm to about 2 mm, or about 1 mm to about 3 mm. In an embodiment, the textured surface 748 may include a plurality of grooves formed therein that extend partially through the fluid impermeable barrier 702.

The grooves formed in the fluid impermeable barrier 702 may be the same or substantially similar to any of the grooves disclosed herein. In an embodiment, the textured surface 748 may include a plurality of perforations that extend partially through the fluid impermeable barrier 702. The perforations formed in the fluid impermeable barrier 702 may be the same or substantially similar to any of the perforations disclosed herein.

Figure 8:
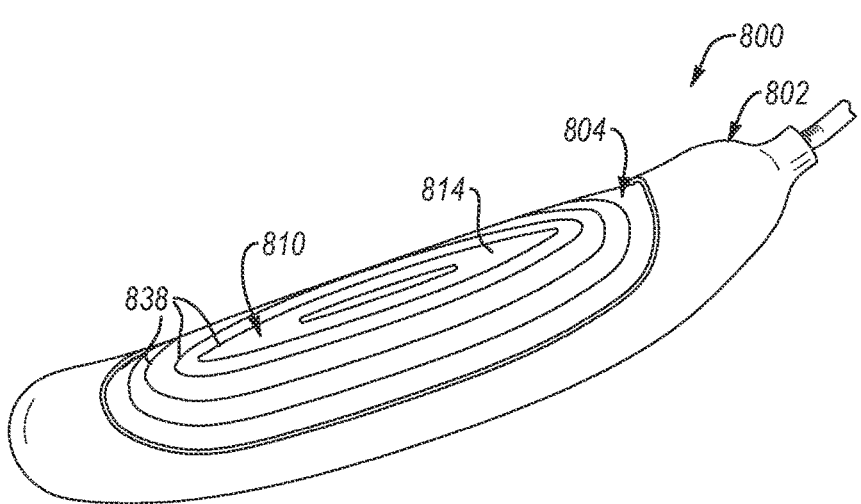
FIGS. 8 and 9 are isometric view of fluid collection assemblies exhibiting different shapes, according to different embodiments.
Figure 9:
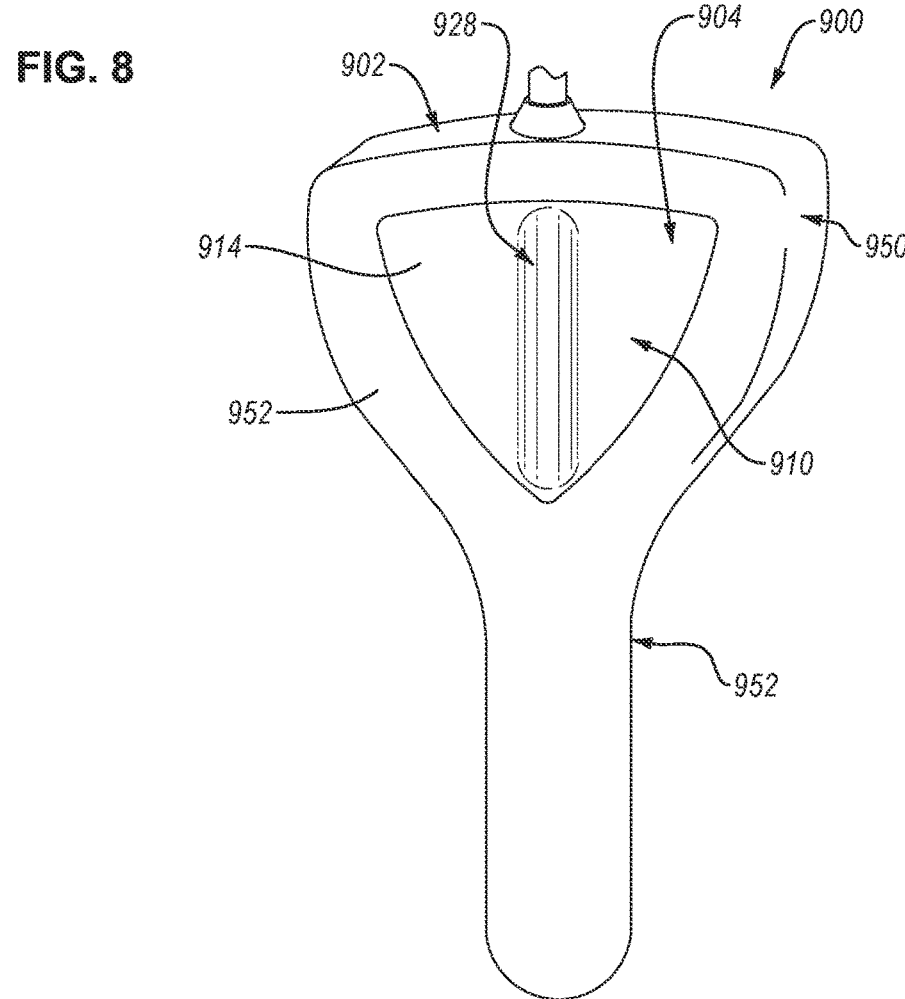

The fluid collection assemblies illustrated in FIGS. 1A-7 exhibit an elongated generally flat shape having a relatively small thickness. As discussed above, fluid collection assemblies exhibiting such shapes exhibit several benefits. However, it is noted that the fluid collection assemblies disclosed herein may exhibit different shapes than the shape illustrated in FIGS. 1A-7. For example, FIGS. 8 and 9 are isometric view of fluid collection assemblies exhibiting different shapes, according to different embodiments. Except as otherwise disclosed herein, the fluid collection assemblies illustrated in FIGS. 8 and 9 are the same or substantially similar to any of the fluid collection assemblies disclosed herein.

Referring to FIG. 8, the fluid collection assembly 800 includes a fluid impermeable barrier 802 defining an opening 804 and a chamber (not shown). The fluid collection assembly 800 also includes a porous material 810 disposed in the chamber that defines a contact surface 814. The fluid collection assembly 800 exhibits a generally cylindrical shape (e.g., a curved generally cylindrical shape). The generally cylindrical shape of the fluid collection assembly 800 allows the fluid collection assembly 800 to fit between the thighs of the individual. Further, due to the cylindrical shape of the fluid collection assembly 800, the contact surface 814 may exhibit a curvature that allows the contact surface 814 to press against the labia folds and may be positionable between the labia folds.

The fluid collection assembly 800 may include any of the movement enhancing features disclosed herein. In an example, the porous material 810 may form a protrusion exhibiting a radius that is less than the radius of the rest of the porous material 810 which, similar to the protrusion 228 of FIGS. 2A and 2B, may allow the protrusion to be more positionable between the labia folds that the rest of the porous material 810.

In an example, the porous material 810 may extend slightly out from the opening 804 similar to the protrusion 328 of FIG. 3. In an example, as illustrated, the porous material 810 may define one or more grooves 838 extending at least partially therethrough, similar to the grooves 438 of FIGS. 4A and 4B. In an example, the porous material 810 may define one or more perforations extending at least partially therethrough that are similar to the perforations 540 of FIGS. 5A and 5B. In an example, the fluid collection assembly 800 may include a fluid permeable element that is attached to the porous material 810 that is similar to the fluid permeable element 642 of FIGS. 6A and 6B. In an example, the fluid impermeable barrier 802 may include a textured surface similar to the textured surface 748 of FIG. 7.

Referring to FIG. 9, the fluid collection assembly 900 includes a fluid impermeable barrier 902 defining an opening 904 and a chamber (not shown). The fluid collection assembly 900 also includes a porous material 910 disposed in the chamber that defines a contact surface 914. The fluid collection assembly 900 includes a fluid receiving portion 950 that includes the portions of the fluid impermeable barrier 902 that defines the opening 904. The urinary collection assembly 900 also includes a longitudinal portion 952 (e.g., elongated portion) extending from the fluid receiving portion 950 formed by a portion of the fluid impermeable barrier 902. The longitudinal portion 952 is configured to be positioned adjacent to or near the perineum of the individual (e.g., positioned between the thighs of the individual).

The fluid receiving portion 950 exhibits a shape that allows the fluid receiving portion 950 to be positioned adjacent to the urethral opening. Generally, a front surface 954 of the fluid receiving portion 950 and the contact surface 914 exhibits a shape that allows the fluid receiving portion 950 to abut the urethral opening. For example, the front surface 954 and the contact surface 914 may exhibit a generally planar topography or may have a concave curved topography which allows the front surface 954 and the contact surface 914 to conform to the vaginal region since the vaginal region is generally planar or has a convex curvature.

The fluid receiving portion 950 may also exhibit a shape that is configured to increase the size of the opening 904 (e.g., the opening 904 generally corresponds to the shape of the fluid receiving portion 950). For example, increasing the size of the fluid receiving portion 950 may allow the fluid receiving portion 950 to define a larger opening 904. The larger opening 904 allows the opening 904 to receive bodily fluids that is emitted from a urethral opening, even when the individual moves in a manner that causes the fluid collection assembly 900 to shift (i.e., the larger opening 904 is a movement enhancing feature). Further, the larger opening 904 allows the opening 904 to receive bodily fluids that would have otherwise leaked between the fluid impermeable barrier 902 and the individual.

In an embodiment, the fluid receiving portion 950 may exhibit a generally triangular shape. The generally triangular shape may allow the fluid receiving portion 950 to correspond to the shape of the groin that surrounds the vaginal region since the groin exhibits a generally triangular shape, especially when the thighs of the individual contact each other. As such, the generally triangular shape of the fluid receiving portion 950 may allow the fluid receiving portion 950 to exhibit the maximum possible size without uncomfortably pressing into the individual. Further, the generally triangular shape of the fluid receiving portion 950 may be movement enhancing features because the generally triangular shape of the fluid receiving portion 950 may substantially occupy the groin thereby preventing the fluid collection assembly 900 from shifting even when the individual moves.

It is noted that the fluid receiving portion 950 may exhibit different shapes than the generally triangular shape illustrated in FIG. 9. For example, the fluid receiving portion 950 may exhibit a generally circular shape, a generally rectangular shape, or any other suitable shape.

The longitudinal portion 952 is distinguishable from the fluid receiving portion 950 based on the widths thereof. For example, in the illustrated embodiment, the width of the fluid receiving portion 950 generally decreases from the maximum width thereof to the longitudinal portion 952 while the width of the longitudinal portion 952 remains substantially constant from the intersection of the fluid receiving portion 950 and the longitudinal portion 952 along at least a portion of a length of the longitudinal portion 952. This may allow the longitudinal portion 952 to fit between the thighs of the individual.

The fluid collection assembly 900 may include any of the movement enhancing features disclosed herein. In an example, as shown, the porous material 910 may form a protrusion 928 similar to the protrusion 228 of FIGS. 2A and 2B. In an example, the porous material 910 may extend slightly out from the opening 904 similar to the protrusion 328 of FIG. 3. In an example, the porous material 910 may define one or more grooves extending at least partially therethrough, similar to the grooves 438 of FIGS. 4A and 4B. In an example, the porous material 910 may define one or more perforations extending at least partially therethrough that are similar to the perforations 540 of FIGS. 5A and 5B. In an example, the fluid collection assembly 900 may include a fluid permeable element that is attached to the porous material 910 that is similar to the fluid permeable element 642 of FIGS. 6A and 6B. In an example, the fluid impermeable barrier 902 may include a textured surface similar to the textured surface 748 of FIG. 7.

Figure 10:
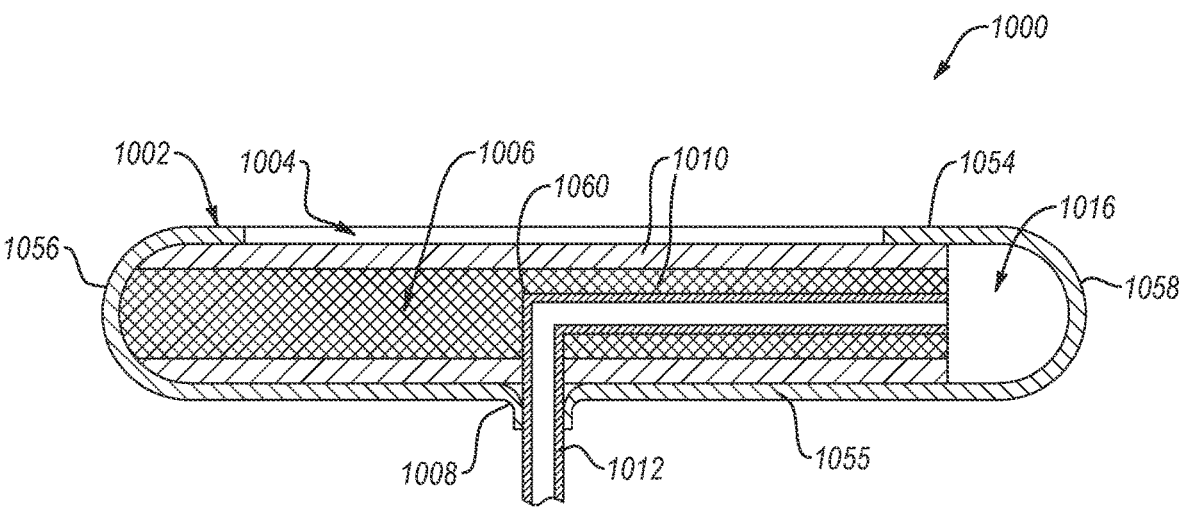
FIG. 10 is a cross-sectional view of a fluid collection assembly including a conduit extending from a back surface of the fluid impermeable barrier, according to an embodiment.

The fluid collection assemblies illustrated in FIGS. 1A-9, the conduit is illustrated as extending away from a distal end of the fluid collection assembly. As such, when the conduit is straight, the conduit and the rest of the fluid collection assembly generally lies in the same plane. However, when the conduit and the rest of the fluid collection assembly are in the same plane, the conduit may act as a lever. As such, any movement in the conduit caused by the individual moving may cause the fluid collection assemblies illustrated in FIGS. 1A-9 to shift since, as a lever, the conduit may act as a force multiplier. As such, in some embodiments, the movement enhancing features of the fluid collection assemblies may include the conduit, when straight, not being in the same plane as the rest of the fluid collection assembly. FIG. 10 is a cross-sectional view of a fluid collection assembly 1000 including a conduit 1012 extending from a back surface 1055 of the fluid impermeable barrier 1002, according to an embodiment. Except as otherwise disclosed herein, the fluid collection assembly 1000 is the same or substantially similar to any of the fluid collection assemblies disclosed herein. For example, the fluid collection assembly 1000 may include a fluid impermeable barrier 1002 that defines an opening 1004, a chamber 1006, a fluid outlet 1008, and a substantially unoccupied fluid reservoir 1016. The fluid collection assembly 1000 may also include a porous material 1010 disposed in the chamber 1006.

The fluid impermeable barrier 1002 includes a distal end 1056 and a proximal end 1058 longitudinally spaced from the distal end 1056. In some embodiments, as shown, the proximal end 1058 may define the fluid reservoir 1016. The fluid impermeable barrier 1002 also includes a front surface 1054 and a back surface 1055 opposite the front surface 1054. The front surface 1054 and the back surface 1055 extend between the distal end 1056 and the proximal end 1058. The front surface 1054 defines the opening 1004 and the back surface 1055 defines the fluid outlet 1008.

The fluid collection assembly 1000 includes a conduit 1012. The conduit 1012 is secured to and extends from the fluid outlet 1008. Since the fluid outlet 1008 is defined by the back surface 1055 of the fluid impermeable barrier 1002, the conduit 1012 extends from the back surface 1055 of the fluid impermeable barrier 1002 instead of the distal end 1056, as shown in FIGS. 1A-9. As such, the conduit 1012 is less likely to act as a lever than the conduits illustrated in FIGS. 1A-9 since the conduit 1012, when straight, does not extend in substantially the same plane as the rest of the fluid collection assembly 1000.

In an embodiment, as shown, the conduit 1012 extends at about a perpendicular angle relative to the portion of the back surface 1055 that defines the fluid outlet 1008. However, in an embodiment, the conduit 1012 may extend from the portion of the back surface 1055 that defines the fluid outlet 1008 at an angle that is about 5° to about 89° (e.g., about 5° to about 45°, about 30° to about 60°, or about 45° to about 89°) or about 91° to about 175° (e.g., about 91° to about 135°, about 120° to about 150°, or about 135° to about 175°).

The conduit 1012 may extend into the chamber 1006. The conduit 1012 may include a bend 1060 therein when the conduit 1012 extends into the chamber 1006 thereby allowing the conduit 1012 to extend further into the chamber 1006. For example, the bend 1060 may allow the conduit 1012 to extend from the fluid outlet 1008 to a location that is adjacent to or within the fluid reservoir 1016. In an embodiment, the bend 1060 is formed in the conduit 1012. In an embodiment, the bend 1060 is a joint that connects a first portion of the conduit 1012 to a second portion of the conduit 1012 that is distinct from the first portion of the conduit 1012. In an embodiment, the bend 1060 is a joint that allows the angle that the conduit 1012 extends from the back surface 1055 to vary.

The vaginal region may exhibit different sizes depending on the individual. A fluid collection assembly that is not configured for the particular size of the vaginal region is more likely shift when the individual moves. As such, in some embodiments, the movement enhancing features of the fluid collection assemblies disclosed herein may include providing a plurality of fluid collection assemblies wherein at least one of the plurality of fluid collection assemblies exhibit a different size. The different size of the plurality of fluid collection assemblies allows a fluid collection assembly to be selected that is better configured for the particular size of the vaginal region than the rest of the fluid collection assemblies. The different sizes of the plurality of fluid collection assemblies may include at least one of a plurality of fluid collection assemblies exhibiting at least one of different lengths, different widths, different thicknesses, or different shapes.

Figure 11:
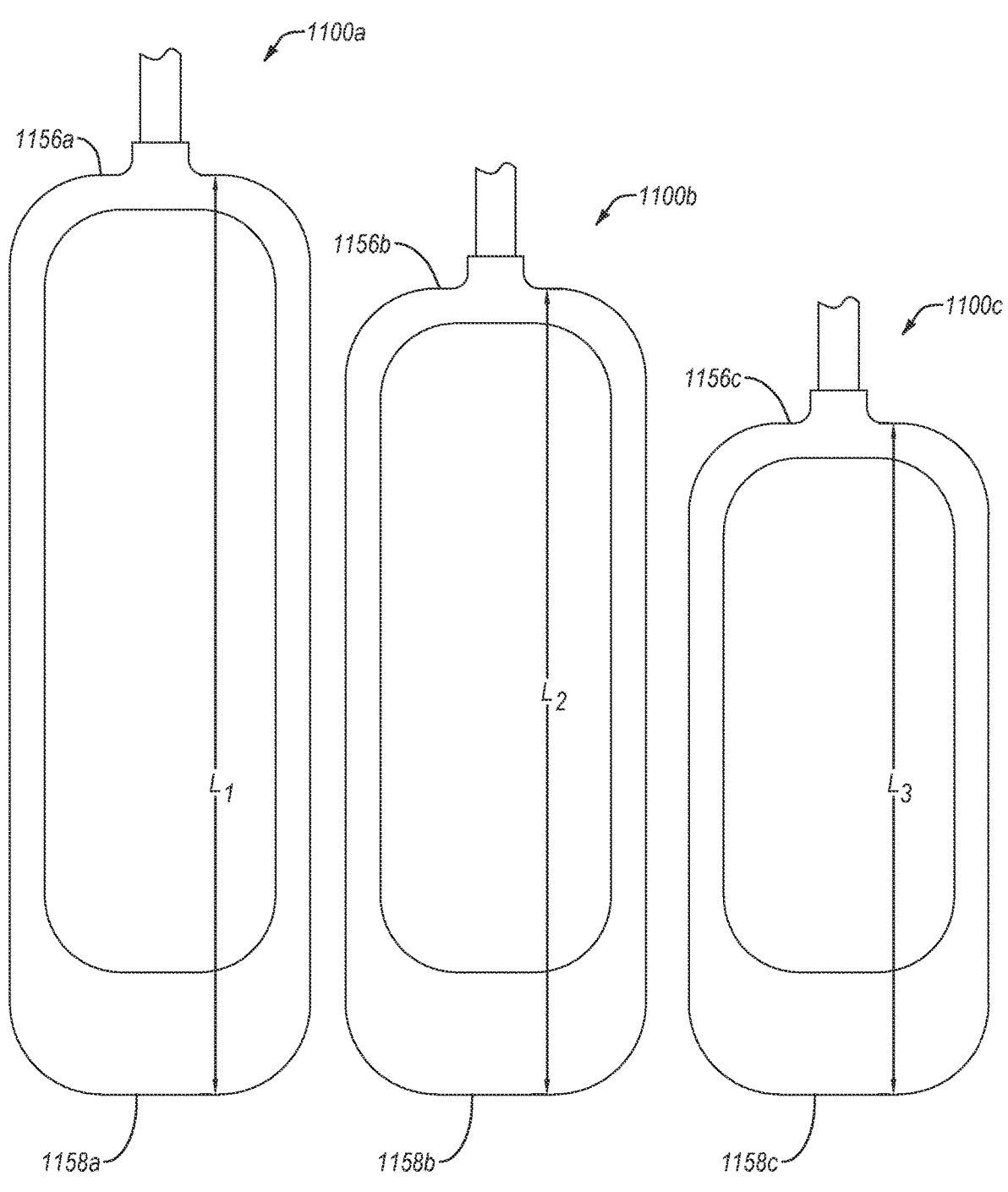
FIG. 11 is a top plan view of a plurality of fluid collection assemblies exhibiting different lengths, according to an embodiment.

FIG. 11 is a top plan view of a plurality of fluid collection assemblies exhibiting different lengths, according to an embodiment. Except as otherwise disclosed herein, each of the plurality of fluid collection assemblies may be the same or substantially similar to any of the fluid collection assemblies disclosed herein. For example, each of the plurality of fluid collection assemblies are illustrated as being substantially similar to the fluid collection assembly 100 illustrated in FIG. 1. However, it is noted that at least one of the plurality of fluid collection assemblies disclosed herein may be similar to any of the other fluid collection assemblies disclosed herein.

In the illustrated embodiment, the plurality of fluid collection assemblies includes a first fluid collection assembly 1100a, a second fluid collection assembly 1100b, and a third fluid collection assembly 1100c. The first fluid collection assembly 1100a exhibits a first length $L_1$ measured from a distal end 1156a to a proximal end 1158a of the fluid impermeable barrier 1102a thereof. The second fluid collection assembly 1100b exhibits a second length $L_2$ measured from a distal end 1156b to a proximal end 1158b of the fluid impermeable barrier 1102b thereof. The third fluid collection assembly 1100c exhibits a third length $L_3$ measured from a distal end 1156c to a proximal end 1158c of the fluid impermeable barrier 1102c thereof. The first length $L_1$ is greater than the second length $L_2$ and the second length $L_2$ is greater than the third length $L_3$.

The individual or a medical practitioner may select one of the first fluid collection assembly 1100a, second fluid collection assembly 1100b, or the third fluid collection assembly 1100c based on the size of the vaginal region. For example, generally, the individual or the medical practitioner may select the fluid collection assembly with the longest length since increasing the length of the fluid collection assembly may decrease the amount of bodily fluids that leaks. However, the fluid collection assembly is more likely to shift when the individual moves if the length is too great. For example, movement of the individual may cause the glutes and/or abdominal muscles to flex and move which may cause the fluid collection assembly to shift if the fluid collection assembly is adjacent to the glutes and/or abdominal muscles. Thus, to allow increased movement of the individual, the individual or the medical practitioner may select one of the first fluid collection assembly 1100a, second fluid collection assembly 1100b, or the third fluid collection assembly 1100c such that the fluid collection assembly is not adjacent to at least one of the glutes and/or the abdominal muscles.

Figure 12:
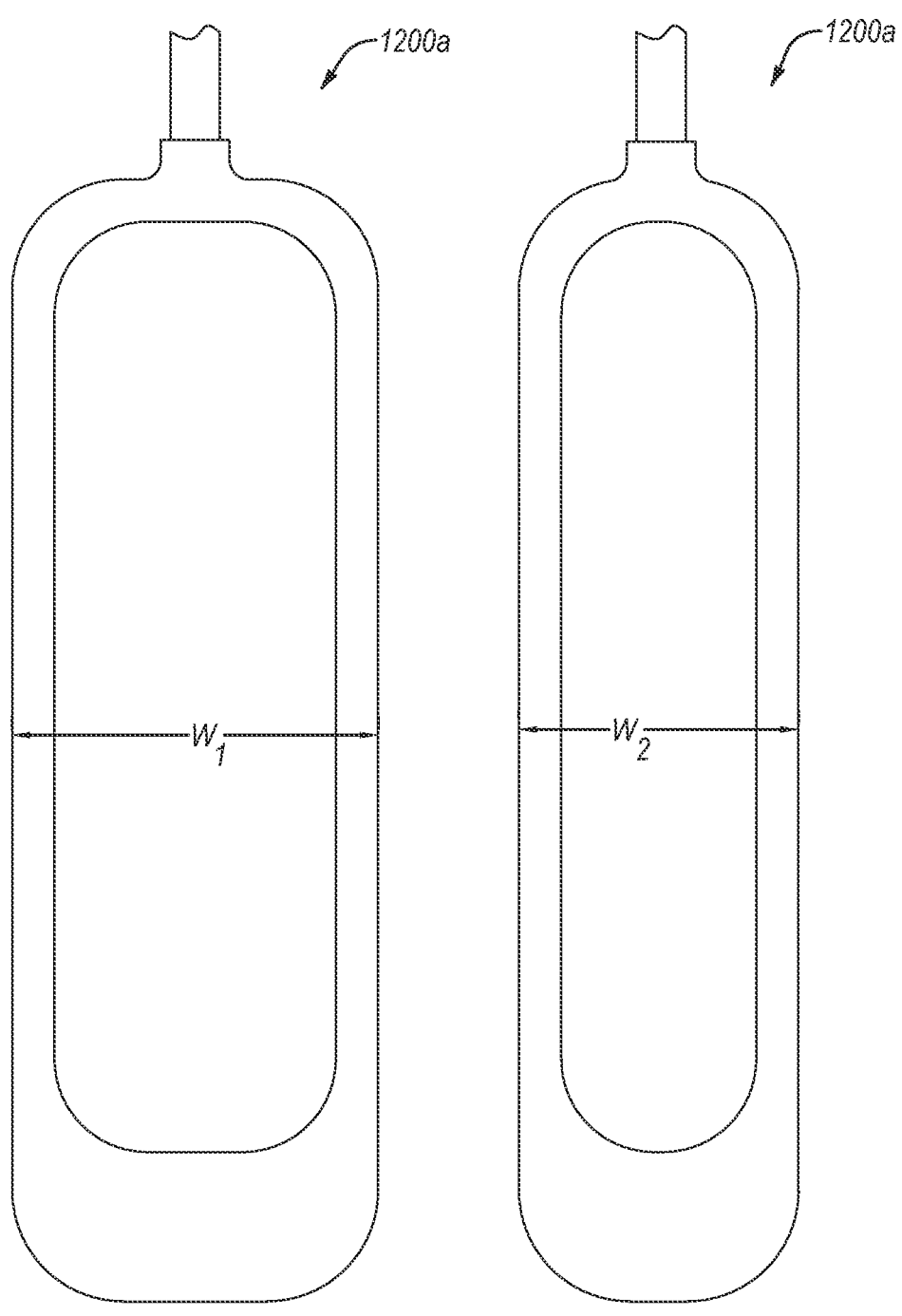
FIG. 12 is a top plan view of a plurality of fluid collection assemblies exhibiting different widths, according to an embodiment.

FIG. 12 is a top plan view of a plurality of fluid collection assemblies exhibiting different widths, according to an embodiment. Except as otherwise disclosed herein, each of the plurality of fluid collection assemblies may be the same or substantially similar to any of the fluid collection assemblies disclosed herein. For example, each of the plurality of fluid collection assemblies are illustrated as being substantially similar to the fluid collection assembly 100 illustrated in FIG. 1. However, it is noted that at least one of the plurality of fluid collection assemblies disclosed herein may include any of the fluid collection assemblies disclosed herein.

In the illustrated embodiment, the plurality of fluid collection assemblies includes a first fluid collection assembly 1200a and a second fluid collection assembly 1200b. The first fluid collection assembly 1200a exhibits a first width $W_1$ measured perpendicularly to a longitudinal length thereof. The second fluid collection assembly 1200b exhibits a second width $W_2$ measured perpendicularly to a longitudinal length thereof. The first width $W_1$ is greater than the second width $W_2$.

The individual or a medical practitioner may select one of the first fluid collection assembly 1200a or the second fluid collection assembly 1200b based on the size of the vaginal region. For example, generally, the individual or the medical practitioner may select the fluid collection assembly with the largest width since increasing the width of the fluid collection assembly may decrease the amount of bodily fluids that leaks. However, movement of the thighs may cause the fluid collection assembly to shift or buckle if the width is too large. Thus, to allow increased movement of the individual, the individual or the medical practitioner may select one of the first fluid collection assembly 1200a or the second fluid collection assembly 1200b based on the size of the vaginal region and, in particular, the space between the thighs.

Figure 13:
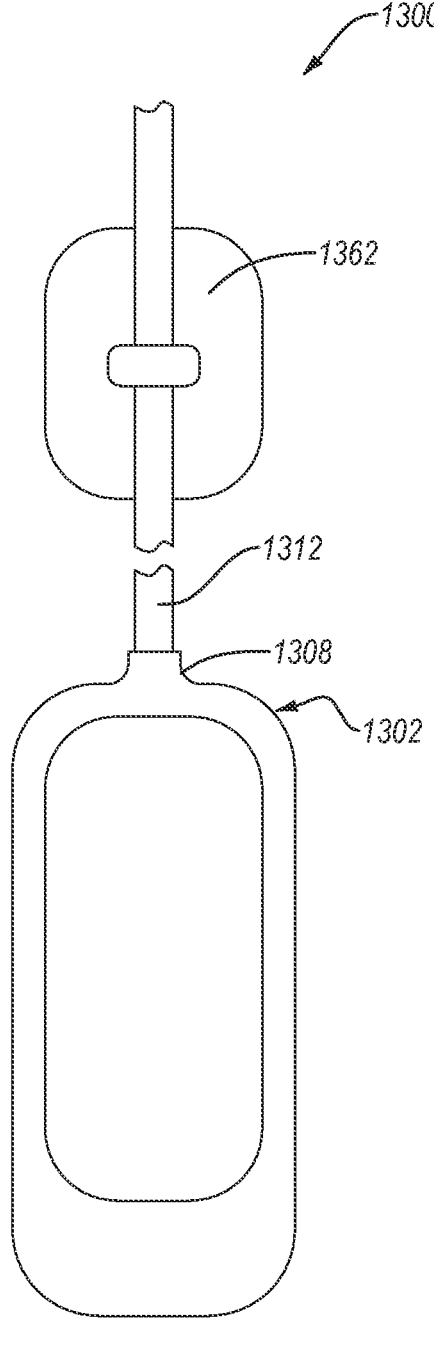
FIG. 13 is a top plan view of a fluid collection assembly that is configured to have the conduit thereof secured to a location that is proximate to the fluid outlet thereof, according to an embodiment.

As previously discussed, the conduit of the fluid collection assemblies disclosed herein may act as levers that cause the fluid collection assembly that includes the conduit to shift when the individual using the fluid collection assembly moves. The conduit is most likely to act as a lever when the conduit, when straight, extends in the same plane as the rest of the fluid collection assembly. However, it is noted that the conduit may still act as a lever when the conduit, when straight, does not extend in the same plane as the rest of the fluid collection assembly though not to the extent as when the conduit extends in the same plane as the rest of the fluid collection assembly. However, securing the conduit to a location that is proximate to the fluid outlet (e.g., the thigh or abdominal region of the individual) may help at least partially mitigate the effect of the conduit acting as a lever. FIG. 13 is a top plan view of a fluid collection assembly 1300 that is configured to have the conduit 1312 thereof secured to a location that is proximate to the fluid outlet 1308 thereof, according to an embodiment. Except as otherwise disclosed herein, the fluid collection assembly 1300 is the same or substantially similar to any of the fluid collection assemblies disclosed herein. For example, the fluid collection assembly 1300 may include a fluid impermeable barrier 1302 defining the fluid outlet 1308 and a conduit 1312 secured to the fluid outlet 1308.

A portion of the conduit 1312 that is spaced (i.e., located downstream) from the fluid permeable barrier 1302 may be configured to be secured to a location that is proximate to (e.g., within about 2 feet, within about 1.5 feet, within about 1 foot, within about 9 inches, within about 6 inches, within about 3 inches, or in ranges of about 1 inch to about 6 inches, about 3 inches to about 9 inches, about 6 inches to about 1 foot, about 9 inches to about 1.5 feet, or about 1 foot to about 2 feet) the fluid outlet 1308. In an embodiment, as illustrated, the portion of the conduit 1312 is secured to the location using with a catheter securement device 1362, such as a STATLOCK® catheter securement device available from C. R. Bard, Inc., including but not limited to those disclosed in U.S. Pat. Nos. 6,117,163; 6,123,398; and 8,211,063, the disclosures of which were previously incorporated herein. In an embodiment, the portion of the conduit 1312 is secured to the location using tape or other suitable device.

The fluid collection assemblies shown in FIGS. 1A-13 are examples of female fluid collection assemblies that are configured to collect bodily fluids from females. However, the fluid collection assemblies, systems, and method disclosed herein may include male fluid collection assemblies shaped, sized, and otherwise configured to collection bodily fluids from males (e.g., collect urine from a male urethral opening).

Figure 14A:
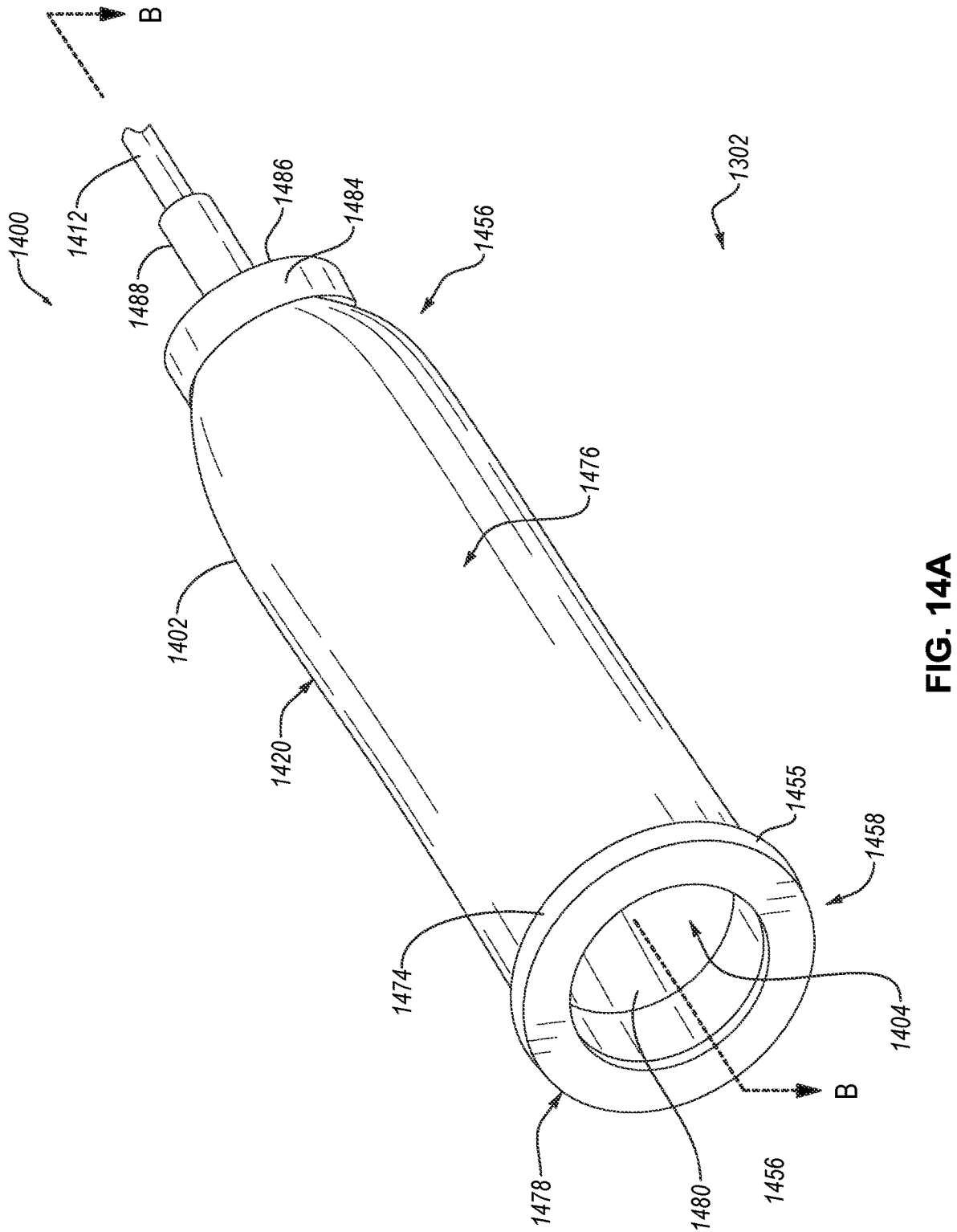
FIG. 14A is an isometric view of a fluid collection assembly, according to an embodiment.
Figure 14B:
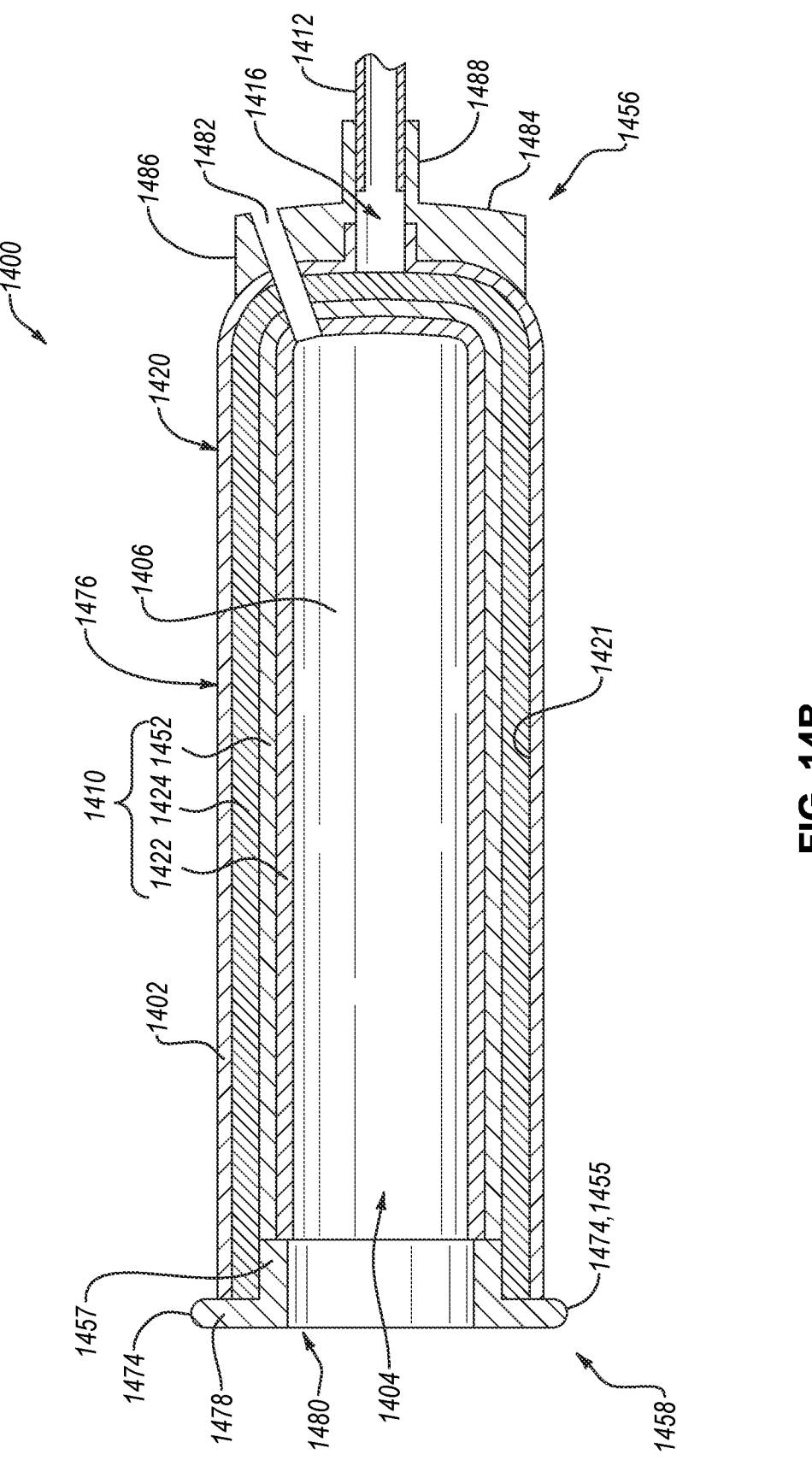
FIG. 14B is a cross-sectional view of the fluid collection assembly of FIG. 14A taken along the plane 14B-14B of FIG. 14A.

FIG. 14A is an isometric view of a fluid collection assembly 1400 according to an embodiment. FIG. 14B is a cross-sectional view of the fluid collection assembly 1400 of FIG. 14A taken along the plane 14B-14B of FIG. 14A, according to an embodiment. Referring to FIG. 14A and FIG. 14B, the fluid collection assembly 1400 includes a receptacle 1474 and a sheath 1476. The receptacle 1474 is sized, shaped, and made of a material to be coupled to skin that surrounds the male urethral opening and have the male urethral opening positioned therethrough. For example, the receptacle 1474 may include an annular base 1478 that defines an opening 1480 in the receptacle 1474. The annular base 1478 is sized and shaped to be positioned around the male urethral opening (e.g., positioned around and/or over the penis) and the opening 1480 may be configured to have the male urethral opening positioned therethrough. The annular base 1478 may also be sized, shaped, made of a material, or otherwise configured to be coupled (e.g., adhesively attached, such as with a hydrogel adhesive) to the skin around the male urethral opening (e.g., around the penis). In an example, the annular base 1478 may exhibit the general shape or contours of the skin surface that the annular base 1478 is selected to be coupled with. The annular base 1478 may be flexible thereby allowing the annular base 1478 to conform to any shape of the skin surface. The annular base 1478 may include a laterally extending flange 1455. The receptacle 1474 also defines a hollowed region that is configured to receive (e.g., seal against) the sheath 1476. For example, the receptacle 1474 may include a longitudinally extending flange 1457 that extends upwardly from the annular base 1478. The longitudinally extending flange 1457 may be tall enough to prevent the sheath 1476 from being accidentally removed from the receptacle 1474 (e.g., at least 0.25 cm tall, 1 cm tall, at least 2.5 cm tall, or at least 5 cm tall). The receptacle 1474 is located at a proximal end 1458 (with respect to a wearer) of the fluid collection assembly 1400.

The sheath 1476 includes (e.g., may be formed from) a fluid impermeable barrier 1402 that is sized and shaped to fit into the hollowed region of the receptacle 1474. For example, the sheath 1476 may be generally tubular or cup-shaped, as shown. The generally tubular or cup-shaped fluid impermeable barrier 1402 may at least partially define the outer surface 1420 of the sheath 1476. The fluid impermeable barrier 1402 may be similar or identical to any of the fluid impermeable barriers disclosed herein, in one or more aspects. For example, the fluid impermeable barrier 1402 may be constructed of any of the materials disclosed herein for the fluid impermeable barrier 1402. The fluid impermeable barrier 1402 at least partially defines the chamber 1406. For example, the inner surface 1421 of the fluid impermeable barrier 1402 at least partially defines the perimeter of the chamber 1406. The chamber 1406 may be similar or identical to any of the chambers disclosed herein in one or more aspects. For example, the chamber 1406 may at least temporarily retain bodily fluids therein. As shown, the fluid collection assembly 1400 may include at least one porous material 1410 therein. The porous material 1410 may be similar or identical to any of the porous materials disclosed herein in one or more aspects. For example, the porous material 1410 may include one or more of a fluid permeable membrane 1422, a fluid permeable support 1424, or an absorbent layer 1452. The fluid impermeable barrier 1402 may also define an opening 1404 extending through the fluid impermeable barrier 1402 that is configured to have a male urethral opening positioned therethrough.

The sheath 1476 and fluid impermeable barrier 1402 may also include at least one vacuum relief hole 1482 that allows the chamber 1406 to remain substantially at atmospheric pressure. The vacuum relief hole 1482 may be located at any point on the sheath 1476, such as near or nearer the opening 1480. In some examples (not shown), the vacuum relief hole 1482 may extend through the cap 1484 or be disposed beneath the cap 1484. In some examples, the fluid collection assembly 1400 may not include the vacuum relief hole 1482, such as when a more complete seal as desired for the chamber 1406.

The sheath 1476 also includes at least a portion of the conduit 1412 therein, such as at least partially disposed in the chamber 1406 of the conduit 1412 only disposed in the fluid outlet 1408. For example, the conduit 1412 may extend from the sheath 1476 at the distal end 1456 to a proximal end 1458 at least proximate to the opening 1480. The proximal end 1458 may be disposed near or on the skin around the male urethral opening (e.g., on the penis or pubic area therearound). Accordingly, when a patient lays on their back, bodily fluids (e.g., urine) may aggregate near the opening 1480 against the skin of the subject. The bodily fluids may be removed from the chamber 1406 via the conduit 1412.

In some examples, the fluid impermeable barrier 1402 may be constructed of a material and/or have a thickness that allows the sheath 1476 to collapse when placed under vacuum, such as to remove air around a penis in the fluid collection assembly 1400 during use. In such examples, the conduit 1412 may extend only to or into the distal end 1456 in the chamber 1406 (e.g., not through to the area adjacent the opening).

In an example, portions of the chamber 1406 may be substantially empty due to the varying sizes and rigidity of the male penis. However, in some examples, the outermost regions of the chamber 1406 (e.g., periphery of the interior regions of the sheath 1476) may include porous material 1410 (e.g., one or more of the fluid permeable membrane 1422 and fluid permeable support 1424). For example, the porous material 1410 may be bonded to the inner surface 1418 of the fluid impermeable barrier 1402. The porous material 1410 may be positioned (e.g., at the distal end of the chamber 1406) to blunt a stream of urine from the male urethral opening thereby limiting splashing and/or to direct the bodily fluids to a selected region of the chamber 1406. Since the chamber 1406 is substantially empty (e.g., substantially all of the chamber 1406 forms a reservoir), the bodily fluids are likely to pool at a gravimetrically low point of the chamber 1406. The gravimetrically low point of the chamber 1406 may be at an intersection of the skin of an individual and the fluid collection assembly 1400, a corner formed in the sheath 1476, or another suitable location depending on the orientation of the wearer.

The porous material 1410 may include one or more of the fluid permeable membrane 1422 or the fluid permeable support 1424. The fluid permeable membrane 1422 and the fluid permeable support 1424 may be similar or identical to any of the fluid permeable membranes or fluid permeable supports as respectively disclosed herein, in one or more aspects such as material make-up or wicking ability. One or more of the fluid permeable membrane 1422 or the fluid permeable support 1424 may be disposed between the fluid impermeable barrier 1402 and a penis inserted into the chamber 1406.

The fluid permeable membrane 1422 may be positioned between the fluid impermeable barrier 1402 and a penis inserted into the chamber 1406, such as between the fluid permeable support 1424 and penis of a wearer as shown. The fluid permeable support 1424 may be positioned between the fluid permeable membrane 1422 and the fluid impermeable barrier 1402. The inner surface 1418, optionally including the end of the chamber 1406 substantially opposite the opening 1404, may be covered with one or both the fluid permeable membrane 1422 or the fluid permeable support 1424. The fluid permeable support 1424 or the fluid permeable membrane 1422 may be affixed (e.g., adhered) to the fluid impermeable barrier 1402. The fluid permeable support 1424 or the fluid permeable membrane 1422 may be affixed to each other. In some examples, the porous material 1410 only includes the fluid permeable membrane 1422 or the fluid permeable support 1424.

In some examples, the fluid collection assembly 1400 includes a cap 1484 at a distal end 1456. The cap 1484 defines an interior channel through which the bodily fluids may be removed from the fluid collection assembly 1400. The interior channel is in fluid communication with the chamber 1406. The cap 1484 may be disposed over at least a portion of the distal end 1456 of one or more of the fluid impermeable barrier 1402 or the porous material 1410. The cap 1484 may be made of a polymer, rubber, or any other fluid impermeable material. The cap 1484 may be attached to one or more of the fluid impermeable barrier 1402, the porous material 1410, or the conduit 1412. The cap 1484 may have a laterally extending flange 1486 and a longitudinally extending flange 1488. The laterally extending flange 1486 may cover at least a portion of the distal end 1456 of the fluid collection assembly 1400. The longitudinally extending flange 1488 may laterally extend a distance from the sheath 1476. The longitudinally extending flange

1472 is sized and configured to receive and fluidly seal against the conduit 1412, such as within the interior channel The conduit 1412 may extend a distance within or through the cap 1484, such as to the porous material 1410, through the porous material 1410, or to a point set-off from the porous material 1410. In the latter example, as depicted in FIG. 14B, the interior channel of the cap 1484 may define a reservoir 1416 therein.

The reservoir 1416 is an unoccupied portion of device such as in the cap 1484 and is void of other material. In some examples, the reservoir 1416 is defined at least partially by the porous material 1410 and the cap 1484. During use, the bodily fluids that are in the chamber 1406 may flow through the porous material 1410 to the reservoir 1416. The reservoir 1416 may store at least some of the bodily fluids therein and/or position the bodily fluids for removal by the conduit 1412. In some examples, at least a portion of the porous material 1410 may extend continuously between at least a portion of the opening of the interior channel and chamber 1406 to move any bodily fluid from the opening directly to the reservoir 1416.

In some examples (not shown), the fluid impermeable barrier 1402 may be disposed on or over the cap 1484, such as enclosing the cap 1484 within the chamber 1406.

In some examples, the sheath 1476 may include at least a portion of the conduit 1412 therein, such as at least partially disposed in the chamber 1406. For example, the conduit 1412 may extend from the sheath 1476 to a region at least proximate to the opening 1480. The inlet of the conduit 1412 may be positioned adjacent to the annular base 1478. The inlet of the conduit 1412 may be positioned to be adjacent or proximate to the gravimetrically low point of the chamber 1406, such as adjacent to the annular base 1478. For example, the inlet may be co-extensive with or offset from the opening 1480. In examples, the inlet may be positioned adjacent to the distal region 1444 of the sheath 1476.

The proximal end 1458 may be disposed near or on the skin around the male urethral opening (e.g., around the penis) and the inlet of the conduit 1412 may be positioned in the proximal end 1458. The outlet of the conduit 1412 may be directly or indirectly coupled to a vacuum source. Accordingly, the bodily fluids may be removed from the proximal end 1458 of the chamber 1406 via the conduit 1412.

The receptacle 1474, the sheath 1476, the cap 1484, and the conduit 1412 may be attached together using any suitable method. For example, at least two of the receptacle 1474, the sheath 1476, the cap 1484, or the conduit 1412 may be attached together using at least one of an interference fit, an adhesive, stitching, welding (e.g., ultrasonic welding), tape, any other suitable method, or combinations thereof.

In some examples (not shown), the fluid collection assembly 1400 may have a one piece design, with one or more of the sheath 1476, the receptacle 1474, and the cap 1484 being a single, integrally formed piece.

Also as shown, the conduit 1412 may be at least partially disposed with the chamber 1406 of a fluid collection assembly 1400. The conduit 1412 may extend from the distal region 1444 to the proximal end 1458. For example, the conduit 1412 may extend through the cap 1484 to a point adjacent to the receptacle 1474. The conduit 1412 is sized and positioned to be coupled to a fluid storage container or the vacuum source (FIG. 10. An outlet of the conduit 1412 may be operably coupled to the vacuum source, directly or indirectly. The inlet (e.g., open terminal end) of the conduit 1412 may be positioned within or adjacent to the chamber 1406 such as at a location expected to be at the gravimetrically low point of the fluid collection assembly 1400 during use. By positioning the inlet in a location expected to be at the gravimetrically low point of the fluid collection assembly 1400 when worn by the user, the bodily fluids introduced into the chamber 1406 may be removed via the conduit 1412 to prevent pooling or stagnation of the fluid within the chamber 1406.

The fluid collection assembly 1400 may include any of the movement enhancing features disclosed herein. In an example, the surface of the porous material 1410 that contacts the penis may include one or more grooves and/or one or more perforations formed therein. In an example, at least a portion of the fluid impermeable barrier 1402 and/or the receptacle 1474 may include a textured surface. In an example, the fluid collection assembly 1400 may be configured such that the conduit 1412 does not, when straight, extend in substantially the same direction and the longitudinal axis of the fluid collection assembly 1400. In an example, the fluid collection assembly 1400 may exhibit a plurality of different sizes.

Further examples of fluid collection assemblies that are configured to collect bodily fluids from males are disclosed in U.S. patent application Ser. No. 16/433,773 filed on Jun. 6, 2019, the disclosure of which is incorporated herein, in its entirety, by this reference.

In some examples, the vacuum source may be remotely located from the fluid collection assembly 1400. In such examples, the conduit 1412 may be fluidly connected to the fluid storage container, which may be disposed between the vacuum source and the fluid collection assembly 1400.

During operation, a male using the fluid collection assembly 1400 may discharge bodily fluids into the chamber 1406. The bodily fluids may pool or otherwise be collected in the chamber 1406. At least some of the bodily fluids may be pulled through the interior of the conduit 1412 via the inlet. The bodily fluids may be drawn out of the fluid collection assembly 1400 via the vacuum/suction provided by the vacuum source. During operation, the aperture 1462 may substantially maintain the pressure in the chamber 1406 at atmospheric pressure even though the bodily fluids are introduced into and subsequently removed from the chamber 1406.

As will be discussed in more detail below, the bodily fluids may be removed from the chamber of the fluid collection assemblies disclosed herein using a vacuum source. For example, the vacuum source may be connected to the conduit and may be configured to apply a suction force to the conduit. The suction force may pull bodily fluids that are present in the chamber into the conduit and pull the bodily fluids through the conduit and into a fluid storage container. The vacuum source may include any suitable vacuum source. However, in some embodiments, the vacuum source may have a fixed location or is otherwise not portable. In such embodiments, the vacuum source may significantly limit the mobility of the individual using the fluid collection assemblies since the fluid collection assembly is tethered to the vacuum source. As such, in some embodiments, the movement enhancing features of the fluid collection assemblies disclosed herein may include attaching the fluid collection assemblies to a portable vacuum source.

Figure 15:
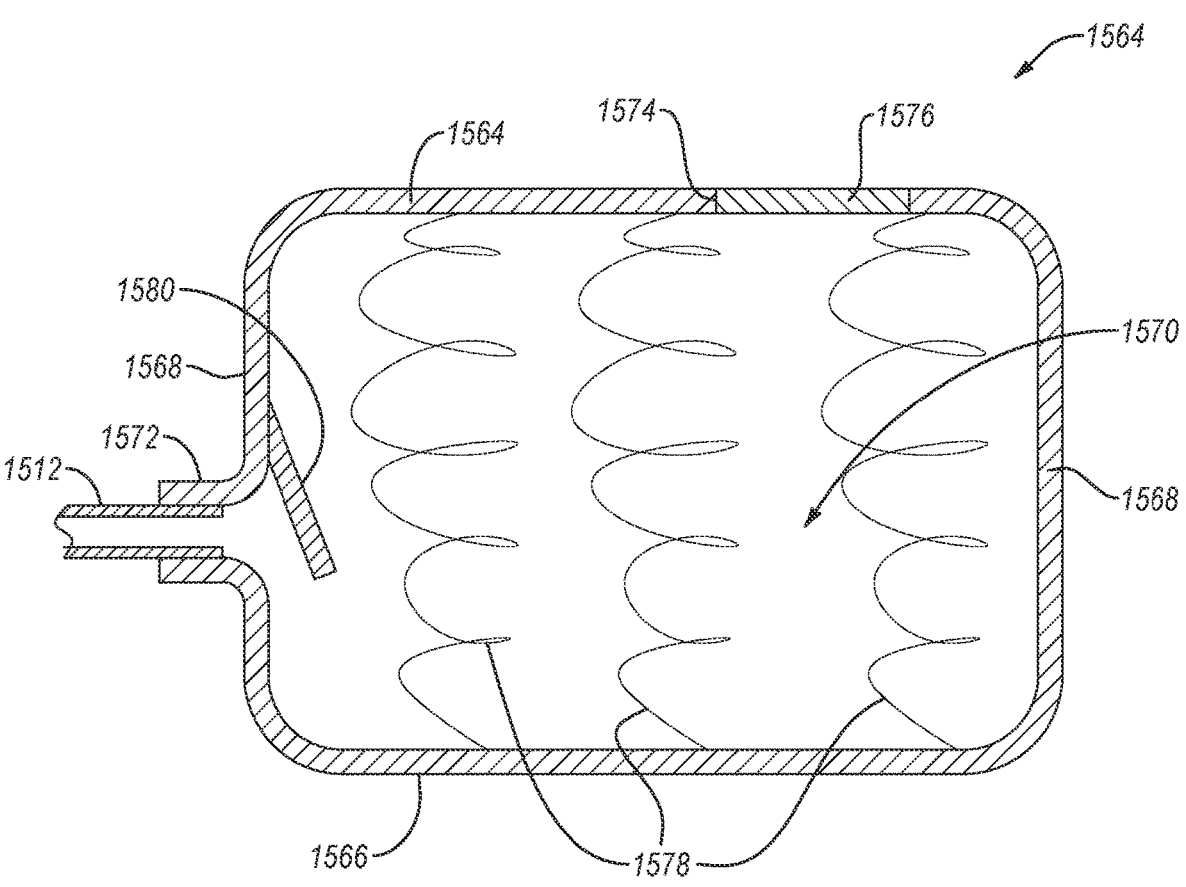
FIG. 15 is a cross-sectional view of a portable vacuum source, according to an embodiment.

FIG. 15 is a schematic cross-sectional view of a portable vacuum source 1562, according to an embodiment. For example, the vacuum source 1562 may be used with any of the fluid collection assemblies disclosed herein. In an embodiment, the vacuum source 1562 includes at least one top wall 1564, at least one bottom wall 1566, and at least one side wall 1568 extending from the top wall 1564 to the bottom wall 1566. The top wall 1564, the bottom wall 1566, and the side wall 1568 define a chamber 1570. At least one of the top wall 1564, the bottom wall 1566, or the side wall 1568 defines a fluid inlet 1572 that is configured to be secured to the conduit 1512. Also, at least one of the top wall 1564, the bottom wall 1566, or the side wall 1568 defines a gas outlet 1574 that is configured to let gas out of the chamber 1570. The gas outlet 1574 may include a gas-permeable/water-impermeable filter 1576 that is configured to allow only gas (and not urine) to flow through the gas outlet 1574. The gas outlet 1574 and/or the filter 1576 may also include a one-way valve (not shown) that only allows the gas to flow from the chamber 1570 to an exterior of the vacuum source 1562 while preventing gas from flowing from the exterior of the vacuum source 1562 to the chamber 1570.

At least the side wall 1568 of the vacuum source 1562 is configured to be compressed (e.g., collapsed, buckled, bent, crumpled, folded, twisted, etc.) by squeezing the vacuum source 1562 with a hand. Compressing the side walls 1548 decreases the volume of the chamber 1570. Gas that is present in the chamber 1570 may escape the chamber 1570 via the gas outlet 1574 when the side wall 1548 is compressed. The vacuum source 1562 includes one or more springs 1578 that are configured expand the volume of the chamber 1570 and decompress the side wall 1548 after the vacuum source 1570 is squeezed. Expanding the volume of the chamber 1570 may apply a suction force to the conduit 1512 which, in turn, may remove bodily fluids from the fluid collection assembly (not shown). The chamber 1570 may be configured to hold the bodily fluids therein such that the vacuum source 1562 is also the fluid storage container.

The vacuum source 1562 may be configured to be squeezed multiple times until the chamber 1570 is completely filled with the bodily fluids. The vacuum source 1562 may include a one-way valve 1580 that is configured to allow bodily fluids to flow from the conduit 1512 to the chamber 1570 and restrict the bodily fluids from flowing from the chamber 1570 to the conduit 1512. As such, squeezing the vacuum source 1562 does not reintroduce the bodily fluids back into the fluid collection assembly which may cause the fluid collection assembly to leak.

Figure 16:
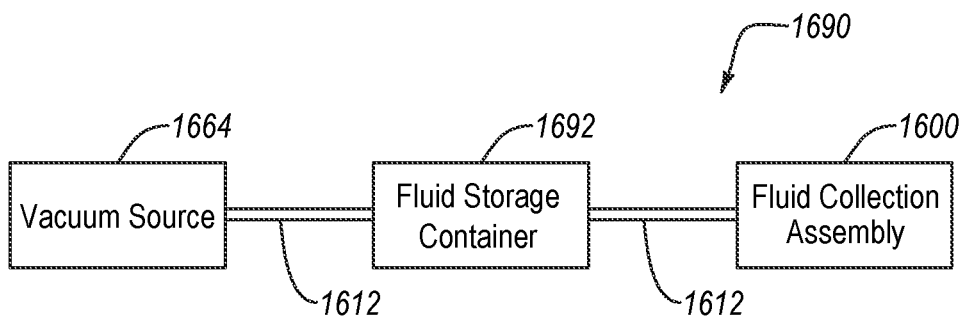
FIG. 16 is a block diagram of a system for fluid collection, according to an embodiment.

FIG. 16 is a block diagram of a system 1690 for fluid collection, according to an embodiment. The system 1690 includes a fluid collection assembly 1600, a fluid storage container 1692, and a vacuum source 1664. The fluid collection assembly 1600, the fluid storage container 1692, and the vacuum source 1664 may be fluidly coupled to each other via one or more conduits 112. For example, fluid collection assembly 1600 may be operably coupled to one or more of the fluid storage container 1692 or the vacuum source 1664 via the conduit 1612. However, as previously discussed, the vacuum source 1664 and the fluid storage container 1692 may be integrally formed together. The bodily fluids collected in the fluid collection assembly 1600 may be removed from the fluid collection assembly 1600 via the conduit 1612 which protrudes into the fluid collection assembly 1600. For example, an inlet of the conduit 1612 may extend into the fluid collection assembly 1600, such as to a fluid reservoir therein. The outlet of the conduit 1612 may extend into the fluid collection assembly 1600 or the vacuum source 1664. Suction force may be introduced into the chamber of the fluid collection assembly 1600 via the inlet of the conduit 1612 responsive to suction (e.g., vacuum) force applied at the outlet of the conduit 1612.

The suction force may be applied to the outlet of the conduit 1612 by the vacuum source 1664 either directly or indirectly. The suction force may be applied indirectly via the fluid storage container 1692. For example, the outlet of the conduit 1612 may be disposed within the fluid storage container 1692 and an additional conduit 1612 may extend from the fluid storage container 1692 to the vacuum source 1664. Accordingly, the vacuum source 1664 may apply suction to the fluid collection assembly 1600 via the fluid storage container 1692. The suction force may be applied directly via the vacuum source 1664. For example, the outlet of the conduit 1612 may be disposed within the vacuum source 1664. An additional conduit 1612 may extend from the vacuum source 1664 to a point outside of the fluid collection assembly 1600, such as to the fluid storage container 1692. In such examples, the vacuum source 1664 may be disposed between the fluid collection assembly 1600 and the fluid storage container 1692.

The fluid collection assemblies 1600 may be similar or identical to any of the fluid collection assemblies disclosed herein in one or more aspects. The fluid collection assembly 1600 may be shaped and sized to be positioned adjacent to a female urethral opening or have a male urethral opening positioned therethrough (e.g., receive a penis therein). For example, the fluid collection assembly 1600 may include a fluid impermeable barrier at least partially defining a chamber (e.g., interior region) of the fluid collection assembly 1600. The fluid impermeable barrier also defines an opening extending therethrough from the external environment. The opening may be positioned adjacent to a female urethral opening or have a male urethral opening positioned therethrough. The fluid collection assembly 1600 may include a fluid permeable membrane disposed within the fluid impermeable barrier. The fluid collection assembly 1600 may include at least one porous material disposed in the chamber such as one or more of a fluid permeable support and a fluid permeable membrane.

The fluid storage container 1692 is sized and shaped to retain the bodily fluids therein. The fluid storage container 1692 may include a bag (e.g., drainage bag), a bottle or cup (e.g., collection jar), or any other enclosed container for storing bodily fluids such as urine. In some examples, the conduit 1612 may extend from the fluid collection assembly 1600 and attach to the fluid storage container 1692 at a first point therein. An additional conduit 1612 may attach to the fluid storage container 1692 at a second point thereon and may extend and attach to the vacuum source 1664. Accordingly, a vacuum (e.g., suction) may be drawn through fluid collection assembly 1600 via the fluid storage container 1692. The bodily fluids, such as urine, may be drained from the fluid collection assembly 1600 using the vacuum source 1664.

The vacuum source 1664 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 1664 may provide a vacuum or suction to remove the bodily fluids from the fluid collection assembly 1600. In some examples, the vacuum source 1664 may be powered by one or more of a power cord (e.g., connected to a power socket), one or more batteries, or even manual power (e.g., a hand operated vacuum pump). In some examples, the vacuum source 1664 may be sized and shaped to fit outside of, on, or within the fluid collection assembly 1600. For example, the vacuum source 1664 may include one or more miniaturized pumps or one or more micro pumps.

The vacuum sources 1664 disclosed herein may include one or more of a switch, a button, a plug, a remote, or any other device suitable to activate the vacuum source 1664.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, +2% or 0% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:
a fluid impermeable barrier defining:
at least one opening;
a chamber in fluid communication with the at least one opening; and
at least one fluid outlet;
at least one porous material disposed in the chamber, the at least one porous material including a fluid permeable membrane extending across the at least one opening, a fluid permeable support, and an additional fluid permeable material positioned between a portion of the fluid permeable membrane extending across the at least one opening and the fluid permeable support; and
one or more movement enhancing features including at least one protrusion that is configured to press against and at least partially fit between labia folds of an individual user thereby allowing increased movement by an individual using the fluid collection assembly without significantly increasing a likelihood that the fluid collection assembly leaks the at least one protrusion at least partially formed by the additional fluid permeable material, the at least one protrusion exhibiting a width that is about 10 mm to about 50 mm.

2. The fluid collection assembly of claim 1, wherein the one or more movement enhancing features include the fluid collection assembly exhibiting a generally elongated flat shape, and wherein the fluid collection assembly includes at least one conduit exhibiting a width and a thickness that is less than the width.

3. The fluid collection assembly of claim 1, wherein the fluid collection assembly exhibits a generally cylindrical shape.

4. The fluid collection assembly of claim 1, wherein the at least one porous material includes a contact surface.

5. The fluid collection assembly of claim 1, wherein the at least one protrusion exhibits a width that is substantially the same as a width of the at least one opening.

6. The fluid collection assembly of claim 4, wherein the contact surface includes one or more grooves extending partially through the at least one porous material.

7. The fluid collection assembly of claim 4, wherein the contact surface includes one or more perforations extending at least partially through the at least one porous material.

8. The fluid collection assembly of claim 1, wherein the one or more movement enhancing features include at least one fluid permeable element attached to the at least one porous material.

9. The fluid collection assembly of claim 1, wherein at least a portion of the fluid impermeable barrier includes a textured surface.

10. The fluid collection assembly of claim 1, wherein the one or more movement enhancing features include the fluid impermeable barrier including a front surface defining the opening and a back surface opposite the front surface, the back surface defining the fluid outlet, and wherein the fluid collection assembly includes at least one conduit extending from the fluid outlet at an angle that is 30° to about 150° relative to the back surface when the at least one conduit is straight.

11. The fluid collection assembly of claim 10, wherein the at least one conduit extends into the chamber and a portion of the at least one conduit that is within the chamber includes at least one bend.

12. A system comprising:

at least one fluid collection assembly including:

a fluid impermeable barrier defining at least one opening, a chamber in fluid communication with the at least one opening, and at least one fluid outlet;

at least one porous material disposed in the chamber, the at least one porous material including a fluid permeable membrane extending across the at least one opening, a fluid permeable support, and an additional fluid permeable material positioned between a portion of the fluid permeable membrane extending across the at least one opening and the fluid permeable support; and one or more movement enhancing features including at least one protrusion that is configured to press against and at least partially fit between the labia folds of an individual user thereby allowing increased movement by an individual using the fluid collection assembly without significantly increasing a likelihood that the fluid collection assembly leaks, the at least one protrusion at least partially formed by the additional fluid permeable material, the at least one protrusion exhibiting a width that is about 10 mm to about 50 mm.

13. The system of claim 12, wherein the at least one fluid collection assembly includes a plurality of the fluid collection assemblies, and wherein at least two of the plurality of the fluid collection assemblies exhibit different lengths.

14. The system of claim 12, wherein the at least one fluid collection assembly includes a plurality of the fluid collection assemblies, and wherein at least two of the plurality of the fluid collection assemblies exhibit different widths.

15. The system of claim 12, further comprising a catheter securement device that is configured to secure a portion of the conduit that is spaced from the fluid impermeable barrier to a location that is proximate to the fluid outlet.

16. The system of claim 12, further comprising a vacuum source in fluid communication with the chamber.

17. The system of claim 16, wherein the vacuum source includes:

at least one top wall;

at least one bottom wall;

at least one side wall extending between the at least one top wall and the at least one bottom wall, the at least one side wall is configured to be compressed when the vacuum source is squeezed;

at least one fluid inlet formed in at least one the at least one top wall, the at least one bottom wall, or the at least one side wall;

at least one gas outlet formed in at least one the at least one top wall, the at least one bottom wall, or the at least one side wall; and a chamber defined by the at least one top wall, the at least one bottom wall, and the at least one side wall.

18. The system of claim 16, further comprising at least one fluid storage container in fluid communication with the fluid collection assembly and the vacuum source.

19. The fluid collection assembly of claim 4, wherein the one or more movement enhancing features include at least one protrusion, the contact surface including the at least one protrusion and a flat portion.

20. The fluid collection assembly of claim 6, wherein the one or more grooves include a plurality of concentric grooves and the one or more grooves are non-intersecting.

* * * * *